United States Patent [19]

Liu

[11] Patent Number: 5,468,634
[45] Date of Patent: Nov. 21, 1995

US005468634A

[54] AXL ONCOGENE

[75] Inventor: Edison T. Liu, Chapel Hill, N.C.

[73] Assignee: The University of North Carolina at Chapel Hill, Chapel Hill, N.C.

[21] Appl. No.: 372,892

[22] Filed: Jan. 13, 1995

Related U.S. Application Data

[63] Continuation of Ser. No. 718,572, Jun. 24, 1991, abandoned.

[51] Int. Cl.$^6$ ............... C12N 15/12; C12N 5/10; C12N 15/85; C12N 15/86
[52] U.S. Cl. ............ 435/240.2; 435/6; 435/172.1; 435/252.3; 435/320.1; 536/23.1; 536/23.5; 436/64
[58] Field of Search ............ 435/6, 91.1, 172.1, 435/172.3, 240.2, 252.3, 270, 320.1; 436/64; 536/23.1, 23.5

[56] References Cited

U.S. PATENT DOCUMENTS

| | | | |
|---|---|---|---|
| 4,535,058 | 8/1985 | Weinberg et al. | 435/6 |
| 4,740,463 | 4/1988 | Weinberg et al. | 435/172.3 |
| 4,786,718 | 11/1988 | Weinberg et al. | 530/387 |
| 4,935,341 | 6/1990 | Bargmann et al. | 435/6 |

FOREIGN PATENT DOCUMENTS

| | | |
|---|---|---|
| 403144 | of 1990 | European Pat. Off. . |
| 413908 | of 1991 | European Pat. Off. . |
| WO89/10412 | of 1989 | WIPO . |
| WO89/06692 | of 1989 | WIPO . |

OTHER PUBLICATIONS

O'Bryan et al, Mol. Cell. Biol., vol. 11, pp. 5016–5031, 1991.
Janssen et al. Oncogene, vol. 6, No. 11, Nov. 1991, pp. 2113–2120.
J. Welch et al., *Biology of Reproduction* 43, 559–568 (1990).
J. Welch and M. O'Rand, *Biology of Reproduction* 43, 569–578 (1990).
Edison Liu et al; *Transforming genes in chronic myelogenous leukemia*, Proc. Natl. Acad. Sci. 85, pp. 1952–1956 (Mar. 1988).

*Primary Examiner*—Mary E. Mosher
*Assistant Examiner*—Laurie Scheiner
*Attorney, Agent, or Firm*—Bell, Seltzer, Park & Gibson

[57] ABSTRACT

Isolated DNA sequences encoding a mammalian axl receptor which exhibits axl oncogene activity are disclosed. Also disclosed are vectors containing such DNA sequences, host cells containing such DNA sequences, axl receptor proteins, and soluble axl receptors, chimeric proteins including the extracellular domain of the axl receptor and DNA sequences encoding such chimeric proteins, and antibodies which specifically bind the axl receptor.

17 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3254 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 159..2840

( x i ) SEQUENCE DESCRIPTION: SEQ ID NO:1:

```
GCTGGGCAGA  GCCGGTGGCA  AGGGCCTCCC  CTGCCGCTGT  GCCAGGCAGG  CAGTGCCAAA       60

TCCGGGGAGC  CTGGAGCTGG  GGGGAGGGCC  GGGGACAGCC  CGGCCCTGCC  CCCTCCCCCG      120

CTGGGAGCCC  AGCAACTTCT  GAGGAAAGTT  TGGCACCC ATG GCG TGG CGG TGC            173
                                            Met Ala Trp Arg Cys
                                             1               5

CCC AGG ATG GGC AGG GTC CCG CTG GCC TGG TGC TTG GCG CTG TGC GGC            221
Pro Arg Met Gly Arg Val Pro Leu Ala Trp Cys Leu Ala Leu Cys Gly
             10                  15                  20

TGG GCG TGC ATG GCC CCC AGG GGC ACG CAG GCT GAA GAA AGT CCC TTC            269
Trp Ala Cys Met Ala Pro Arg Gly Thr Gln Ala Glu Glu Ser Pro Phe
             25                  30                  35

GTG GGC AAC CCA GGG AAT ATC ACA GGT GCC CGG GGA CTC ACG GGC ACC            317
Val Gly Asn Pro Gly Asn Ile Thr Gly Ala Arg Gly Leu Thr Gly Thr
             40                  45                  50

CTT CGG TGT CAG CTC CAG GTT CAG GGA GAG CCC CCC GAG GTA CAT TGG            365
Leu Arg Cys Gln Leu Gln Val Gln Gly Glu Pro Pro Glu Val His Trp
     55                  60                  65

CTT CGG GAT GGA CAG ATC CTG GAG CTC GCG GAC AGC ACC CAG ACC CAG            413
Leu Arg Asp Gly Gln Ile Leu Glu Leu Ala Asp Ser Thr Gln Thr Gln
 70                  75                  80                  85

GTG CCC CTG GGT GAG GAT GAA CAG GAT GAC TGG ATA GTG GTC AGC CAG            461
Val Pro Leu Gly Glu Asp Glu Gln Asp Asp Trp Ile Val Val Ser Gln
                 90                  95                 100

CTC AGA ATC ACC TCC CTG CAG CTT TCC GAC ACG GGA CAG TAC CAG TGT            509
Leu Arg Ile Thr Ser Leu Gln Leu Ser Asp Thr Gly Gln Tyr Gln Cys
             105                 110                 115
```

| | | | | | | | | | | | | | | | | |
|---|---|---|---|---|---|---|---|---|---|---|---|---|---|---|---|---|
| TTG | GTG | TTT | CTG | GGA | CAT | CAG | ACC | TTC | GTG | TCC | CAG | CCT | GGC | TAT | GTT | 557 |
| Leu | Val | Phe 120 | Leu | Gly | His | Gln 125 | Thr | Phe | Val | Ser | Gln 130 | Pro | Gly | Tyr | Val | |
| GGG | CTG | GAG | GGC | TTG | CCT | TAC | TTC | CTG | GAG | GAG | CCC | GAA | GAC | AGG | ACT | 605 |
| Gly | Leu 135 | Glu | Gly | Leu | Pro | Tyr 140 | Phe | Leu | Glu | Glu | Pro 145 | Glu | Asp | Arg | Thr | |
| GTG | GCC | GCC | AAC | ACC | CCC | TTC | AAC | CTG | AGC | TGC | CAA | GCT | CAG | GGA | CCC | 653 |
| Val 150 | Ala | Ala | Asn | Thr | Pro 155 | Phe | Asn | Leu | Ser | Cys 160 | Gln | Ala | Gln | Gly | Pro 165 | |
| CCA | GAG | CCC | GTG | GAC | CTA | CTC | TGG | CTC | CAG | GAT | GCT | GTC | CCC | CTG | GCC | 701 |
| Pro | Glu | Pro | Val | Asp 170 | Leu | Leu | Trp | Leu | Gln 175 | Asp | Ala | Val | Pro | Leu 180 | Ala | |
| ACG | GCT | CCA | GGT | CAC | GGC | CCC | CAG | CGC | AGC | CTG | CAT | GTT | CCA | GGG | CTG | 749 |
| Thr | Ala | Pro | Gly 185 | His | Gly | Pro | Gln | Arg 190 | Ser | Leu | His | Val | Pro 195 | Gly | Leu | |
| AAC | AAG | ACA | TCC | TCT | TTC | TCC | TGC | GAA | GCC | CAT | AAC | GCC | AAG | GGG | GTC | 797 |
| Asn | Lys | Thr 200 | Ser | Ser | Phe | Ser | Cys 205 | Glu | Ala | His | Asn | Ala 210 | Lys | Gly | Val | |
| ACC | ACA | TCC | CGC | ACA | GCC | ACC | ATC | ACA | GTG | CTC | CCC | CAG | CAG | CCC | CGT | 845 |
| Thr | Thr | Ser | Arg | Thr 215 | Ala | Thr | Ile | Thr | Val 220 | Leu | Pro | Gln | Gln | Pro 225 | Arg | |
| AAC | CTC | CAC | CTG | GTC | TCC | CGC | CAA | CCC | ACG | GAG | CTG | GAG | GTG | GCT | TGG | 893 |
| Asn | Leu | His | Leu | Val 230 | Ser | Arg | Gln | Pro | Thr 235 | Glu | Leu | Glu | Val | Ala 240 | Trp 245 | |
| ACT | CCA | GGC | CTG | AGC | GGC | ATC | TAC | CCC | CTG | ACC | CAC | TGC | ACC | CTG | CAG | 941 |
| Thr | Pro | Gly | Leu | Ser 250 | Gly | Ile | Tyr | Pro | Leu 255 | Thr | His | Cys | Thr | Leu 260 | Gln | |
| GCT | GTG | CTG | TCA | GAC | GAT | GGG | ATG | GGC | ATC | CAG | GCG | GGA | GAA | CCA | GAC | 989 |
| Ala | Val | Leu | Ser 265 | Asp | Asp | Gly | Met | Gly 270 | Ile | Gln | Ala | Gly | Glu 275 | Pro | Asp | |
| CCC | CCA | GAG | GAG | CCC | CTC | ACC | TCG | CAA | GCA | TCC | GTG | CCC | CCC | CAT | CAG | 1037 |
| Pro | Pro | Glu 280 | Glu | Pro | Leu | Thr | Ser 285 | Gln | Ala | Ser | Val | Pro 290 | Pro | His | Gln | |
| CTT | CGG | CTA | GGC | AGC | CTC | CAT | CCT | CAC | ACC | CCT | TAT | CAC | ATC | CGC | GTG | 1085 |
| Leu | Arg 295 | Leu | Gly | Ser | Leu | His 300 | Pro | His | Thr | Pro | Tyr 305 | His | Ile | Arg | Val | |
| GCA | TGC | ACC | AGC | AGC | CAG | GGC | CCC | TCA | TCC | TGG | ACC | CAC | TGG | CTT | CCT | 1133 |
| Ala 310 | Cys | Thr | Ser | Ser | Gln 315 | Gly | Pro | Ser | Ser | Trp 320 | Thr | His | Trp | Leu | Pro 325 | |
| GTG | GAG | ACG | CCG | GAG | GGA | GTG | CCC | CTG | GGC | CCC | CCT | GAG | AAC | ATT | AGT | 1181 |
| Val | Glu | Thr | Pro | Glu 330 | Gly | Val | Pro | Leu | Gly 335 | Pro | Pro | Glu | Asn | Ile 340 | Ser | |
| GCT | ACG | CGG | AAT | GGG | AGC | CAG | GCC | TTC | GTG | CAT | TGG | CAA | GAG | CCC | CGG | 1229 |
| Ala | Thr | Arg | Asn 345 | Gly | Ser | Gln | Ala | Phe 350 | Val | His | Trp | Gln | Glu 355 | Pro | Arg | |
| GCG | CCC | CTG | CAG | GGT | ACC | CTG | TTA | GGG | TAC | CGG | CTG | GCG | TAT | CAA | GGC | 1277 |
| Ala | Pro | Leu | Gln 360 | Gly | Thr | Leu | Leu | Gly 365 | Tyr | Arg | Leu | Ala | Tyr 370 | Gln | Gly | |
| CAG | GAC | ACC | CCA | GAG | GTG | CTA | ATG | GAC | ATA | GGG | CTA | AGG | CAA | GAG | GTG | 1325 |
| Gln | Asp | Thr 375 | Pro | Glu | Val | Leu | Met 380 | Asp | Ile | Gly | Leu | Arg 385 | Gln | Glu | Val | |
| ACC | CTG | GAG | CTG | CAG | GGG | GAC | GGG | TCT | GTG | TCC | AAT | CTG | ACA | GTG | TGT | 1373 |
| Thr | Leu | Glu 390 | Leu | Gln | Gly | Asp | Gly 395 | Ser | Val | Ser | Asn | Leu 400 | Thr | Val | Cys 405 | |
| GTG | GCA | GCC | TAC | ACT | GCT | GCT | GGG | GAT | GGA | CCC | TGG | AGC | CTC | CCA | GTA | 1421 |
| Val | Ala | Ala | Tyr | Thr 410 | Ala | Ala | Gly | Asp | Gly 415 | Pro | Trp | Ser | Leu | Pro 420 | Val | |
| CCC | CTG | GAG | GCC | TGG | CGC | CCA | GGG | CAA | GCA | CAG | CCA | GTC | CAC | CAG | CTG | 1469 |
| Pro | Leu | Glu | Ala | Trp | Arg | Pro | Gly | Gln | Ala | Gln | Pro | Val | His | Gln | Leu | |

|  |  |  |  |  |  |  |  |  |  |  |  |  |  |  |  |
|---|---|---|---|---|---|---|---|---|---|---|---|---|---|---|---|
| GTG | AAG | GAA | CCT | TCA | ACT | CCT | GCC | TTC | TCG | TGG | CCC | TGG | TGG | TAT | GTA | 1517
| Val | Lys | Glu | Pro | Ser | Thr | Pro | Ala | Phe | Ser | Trp | Pro | Trp | Trp | Tyr | Val |
|  |  | 440 |  |  |  | 445 |  |  |  | 450 |  |  |  |  |  |
| CTG | CTA | GGA | GCA | GTC | GTG | GCC | GCT | GCC | TGT | GTC | CTC | ATC | TTG | GCT | CTC | 1565
| Leu | Leu | Gly | Ala | Val | Val | Ala | Ala | Ala | Cys | Val | Leu | Ile | Leu | Ala | Leu |
|  | 455 |  |  |  | 460 |  |  |  |  | 465 |  |  |  |  |  |
| TTC | CTT | GTC | CAC | CGG | CGA | AAG | AAG | GAG | ACC | CGT | TAT | GGA | GAA | GTG | TTT | 1613
| Phe | Leu | Val | His | Arg | Arg | Lys | Lys | Glu | Thr | Arg | Tyr | Gly | Glu | Val | Phe |
| 470 |  |  |  | 475 |  |  |  | 480 |  |  |  |  |  | 485 |  |
| GAA | CCA | ACA | GTG | GAA | AGA | GGT | GAA | CTG | GTA | GTC | AGG | TAC | CGC | GTG | CGC | 1661
| Glu | Pro | Thr | Val | Glu | Arg | Gly | Glu | Leu | Val | Val | Arg | Tyr | Arg | Val | Arg |
|  |  |  |  | 490 |  |  |  | 495 |  |  |  |  | 500 |  |  |
| AAG | TCC | TAC | AGT | CGT | CGG | ACC | ACT | GAA | GCT | ACC | TTG | AAC | AGC | CTG | GGC | 1709
| Lys | Ser | Tyr | Ser | Arg | Arg | Thr | Thr | Glu | Ala | Thr | Leu | Asn | Ser | Leu | Gly |
|  |  |  | 505 |  |  |  |  | 510 |  |  |  |  | 515 |  |  |
| ATC | AGT | GAA | GAG | CTG | AAG | GAG | AAG | CTG | CGG | GAT | GTG | ATG | GTG | GAC | CGG | 1757
| Ile | Ser | Glu | Glu | Leu | Lys | Glu | Lys | Leu | Arg | Asp | Val | Met | Val | Asp | Arg |
|  |  | 520 |  |  |  | 525 |  |  |  |  | 530 |  |  |  |  |
| CAC | AAG | GTG | GCC | CTG | GGG | AAG | ACT | CTG | GGA | GAG | GGA | GAG | TTT | GGA | GCT | 1805
| His | Lys | Val | Ala | Leu | Gly | Lys | Thr | Leu | Gly | Glu | Gly | Glu | Phe | Gly | Ala |
|  | 535 |  |  |  | 540 |  |  |  |  | 545 |  |  |  |  |  |
| GTG | ATG | GAA | GGC | CAG | CTC | AAC | CAG | GAC | GAC | TCC | ATC | CTC | AAG | GTG | GCT | 1853
| Val | Met | Glu | Gly | Gln | Leu | Asn | Gln | Asp | Asp | Ser | Ile | Leu | Lys | Val | Ala |
| 550 |  |  |  |  | 555 |  |  |  |  | 560 |  |  |  |  | 565 |
| GTG | AAG | ACG | ATG | AAG | ATT | GCC | ATC | TGC | ACG | AGG | TCA | GAG | CTG | GAG | GAT | 1901
| Val | Lys | Thr | Met | Lys | Ile | Ala | Ile | Cys | Thr | Arg | Ser | Glu | Leu | Glu | Asp |
|  |  |  |  | 570 |  |  |  | 575 |  |  |  |  | 580 |  |  |
| TTC | CTG | AGT | GAA | GCG | GTC | TGC | ATG | AAG | GAA | TTT | GAC | CAT | CCC | AAC | GTC | 1949
| Phe | Leu | Ser | Glu | Ala | Val | Cys | Met | Lys | Glu | Phe | Asp | His | Pro | Asn | Val |
|  |  |  | 585 |  |  |  |  | 590 |  |  |  |  | 595 |  |  |
| ATG | AGG | CTC | ATT | GGT | GTC | TGT | TTC | CAG | GGT | TCT | GAA | CGA | GAG | AGC | TTC | 1997
| Met | Arg | Leu | Ile | Gly | Val | Cys | Phe | Gln | Gly | Ser | Glu | Arg | Glu | Ser | Phe |
|  |  | 600 |  |  |  | 605 |  |  |  |  | 610 |  |  |  |  |
| CCA | GCA | CCT | GTG | GTC | ATC | TTA | CCT | TTC | ATG | AAA | CAT | GGA | GAC | CTA | CAC | 2045
| Pro | Ala | Pro | Val | Val | Ile | Leu | Pro | Phe | Met | Lys | His | Gly | Asp | Leu | His |
|  | 615 |  |  |  | 620 |  |  |  |  | 625 |  |  |  |  |  |
| AGC | TTC | CTC | CTC | TAT | TCC | CGG | CTC | GGG | GAC | CAG | CCA | GTG | TAC | CTG | CCC | 2093
| Ser | Phe | Leu | Leu | Tyr | Ser | Arg | Leu | Gly | Asp | Gln | Pro | Val | Tyr | Leu | Pro |
| 630 |  |  |  |  | 635 |  |  |  |  | 640 |  |  |  |  | 645 |
| ACT | CAG | ATG | CTA | GTG | AAG | TTC | ATG | GCA | GAC | ATC | GCC | AGT | GGC | ATG | GAG | 2141
| Thr | Gln | Met | Leu | Val | Lys | Phe | Met | Ala | Asp | Ile | Ala | Ser | Gly | Met | Glu |
|  |  |  |  | 650 |  |  |  | 655 |  |  |  |  | 660 |  |  |
| TAT | CTG | AGT | ACC | AAG | AGA | TTC | ATA | CAC | CGG | GAC | CTG | GCG | GCC | AGG | AAC | 2189
| Tyr | Leu | Ser | Thr | Lys | Arg | Phe | Ile | His | Arg | Asp | Leu | Ala | Ala | Arg | Asn |
|  |  |  | 665 |  |  |  |  | 670 |  |  |  |  | 675 |  |  |
| TGC | ATG | CTG | AAT | GAG | AAC | ATG | TCC | GTG | TGT | GTG | GCG | GAC | TTC | GGG | CTC | 2237
| Cys | Met | Leu | Asn | Glu | Asn | Met | Ser | Val | Cys | Val | Ala | Asp | Phe | Gly | Leu |
|  |  | 680 |  |  |  | 685 |  |  |  |  | 690 |  |  |  |  |
| TCC | AAG | AAG | ATC | TAC | AAT | GGG | GAC | TAC | TAC | CGC | CAG | GGA | CGT | ATC | GCC | 2285
| Ser | Lys | Lys | Ile | Tyr | Asn | Gly | Asp | Tyr | Tyr | Arg | Gln | Gly | Arg | Ile | Ala |
|  | 695 |  |  |  | 700 |  |  |  |  | 705 |  |  |  |  |  |
| AAG | ATG | CCA | GTC | AAG | TGG | ATT | GCC | ATT | GAG | AGT | CTA | GCT | GAC | CGT | GTC | 2333
| Lys | Met | Pro | Val | Lys | Trp | Ile | Ala | Ile | Glu | Ser | Leu | Ala | Asp | Arg | Val |
| 710 |  |  |  |  | 715 |  |  |  |  | 720 |  |  |  |  | 725 |
| TAC | ACC | AGC | AAG | AGC | GAT | GTG | TGG | TCC | TTC | GGG | GTG | ACA | ATG | TGG | GAG | 2381
| Tyr | Thr | Ser | Lys | Ser | Asp | Val | Trp | Ser | Phe | Gly | Val | Thr | Met | Trp | Glu |
|  |  |  |  | 730 |  |  |  | 735 |  |  |  |  | 740 |  |  |
| ATT | GCC | ACA | AGA | GGC | CAA | ACC | CCA | TAT | CCG | GGC | GTG | GAG | AAC | AGC | GAG | 2429

```
Ile Ala Thr Arg Gly Gln Thr Pro Tyr Pro Gly Val Glu Asn Ser Glu
            745                 750                 755

ATT TAT GAC TAT CTG CGC CAG GGA AAT CGC CTG AAG CAG CCT GCG GAC      2477
Ile Tyr Asp Tyr Leu Arg Gln Gly Asn Arg Leu Lys Gln Pro Ala Asp
        760                 765                 770

TGT CTG GAT GGA CTG TAT GCC TTG ATG TCG CGG TGC TGG GAG CTA AAT      2525
Cys Leu Asp Gly Leu Tyr Ala Leu Met Ser Arg Cys Trp Glu Leu Asn
        775                 780                 785

CCC CAG GAC CGG CCA AGT TTT ACA GAG CTG CGG GAA GAT TTG GAG AAC      2573
Pro Gln Asp Arg Pro Ser Phe Thr Glu Leu Arg Glu Asp Leu Glu Asn
790                 795                 800                 805

ACA CTG AAG GCC TTG CCT CCT GCC CAG GAG CCT GAC GAA ATC CTC TAT      2621
Thr Leu Lys Ala Leu Pro Pro Ala Gln Glu Pro Asp Glu Ile Leu Tyr
                810                 815                 820

GTC AAC ATG GAT GAG GGT GGA GGT TAT CCT GAA CCC CCT GGA GCT GCA      2669
Val Asn Met Asp Glu Gly Gly Gly Tyr Pro Glu Pro Pro Gly Ala Ala
                825                 830                 835

GGA GGA GCT GAC CCC CCA ACC CAG CCA GAC CCT AAG GAT TCC TGT AGC      2717
Gly Gly Ala Asp Pro Pro Thr Gln Pro Asp Pro Lys Asp Ser Cys Ser
        840                 845                 850

TGC CTC ACT GCG GCT GAG GTC CAT CCT GCT GGA CGC TAT GTC CTC TGC      2765
Cys Leu Thr Ala Ala Glu Val His Pro Ala Gly Arg Tyr Val Leu Cys
        855                 860                 865

CCT TCC ACA ACC CCT AGC CCC GCT CAG CCT GCT GAT AGG GGC TCC CCA      2813
Pro Ser Thr Thr Pro Ser Pro Ala Gln Pro Ala Asp Arg Gly Ser Pro
870                 875                 880                 885

GCA GCC CCA GGG CAG GAG GAT GGT GCC TGAGACAACC CTCCACCTGG            2860
Ala Ala Pro Gly Gln Glu Asp Gly Ala
                890

TACTCCCTCT CAGGATCCAA GCTAAGCACT GCCACTGGGG AAAACTCCAC CTTCCCACTT    2920
TCCCACCCCA CGCCTTATCC CCACTTGCAG CCCTGTCTTC CTACCTATCC CACCTCCATC    2980
CCAGACAGGT CCCTCCCCTT CTCTGTGCAG TAGCATCACC TTGAAAGCAG TAGCATCACC    3040
ATCTGTAAAA GGAAGGGGTT GGATTGCAAT ATCTGAAGCC CTCCAGGTG TTAACATTCC     3100
AAGACTCTAG AGTCCAAGGT TTAAAGAGTC TAGATTCAAA GGTTCTAGGT TTCAAAGATG    3160
CTGTGAGTCT TTGGTTCTAA GGACCTGAAA TTCCAAAGTC TCTAATTCTA TTAAAGTGCT    3220
AAGGTTCTAA AAAAAAAAAA AAAAAAAAAA AAAA                                3254
```

( 2 ) INFORMATION FOR SEQ ID NO:2:

( i ) SEQUENCE CHARACTERISTICS:
        ( A ) LENGTH: 894 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80
```

```
Ser  Thr  Gln  Thr  Gln  Val  Pro  Leu  Gly  Glu  Asp  Glu  Gln  Asp  Asp  Trp
               85                       90                      95

Ile  Val  Val  Ser  Gln  Leu  Arg  Ile  Thr  Ser  Leu  Gln  Leu  Ser  Asp  Thr
               100                      105                     110

Gly  Gln  Tyr  Gln  Cys  Leu  Val  Phe  Leu  Gly  His  Gln  Thr  Phe  Val  Ser
               115                      120                     125

Gln  Pro  Gly  Tyr  Val  Gly  Leu  Glu  Gly  Leu  Pro  Tyr  Phe  Leu  Glu  Glu
     130                      135                     140

Pro  Glu  Asp  Arg  Thr  Val  Ala  Ala  Asn  Thr  Pro  Phe  Asn  Leu  Ser  Cys
145                      150                     155                      160

Gln  Ala  Gln  Gly  Pro  Pro  Glu  Pro  Val  Asp  Leu  Leu  Trp  Leu  Gln  Asp
               165                      170                     175

Ala  Val  Pro  Leu  Ala  Thr  Ala  Pro  Gly  His  Gly  Pro  Gln  Arg  Ser  Leu
               180                      185                     190

His  Val  Pro  Gly  Leu  Asn  Lys  Thr  Ser  Ser  Phe  Ser  Cys  Glu  Ala  His
               195                      200                     205

Asn  Ala  Lys  Gly  Val  Thr  Thr  Ser  Arg  Thr  Ala  Thr  Ile  Thr  Val  Leu
     210                      215                     220

Pro  Gln  Gln  Pro  Arg  Asn  Leu  His  Leu  Val  Ser  Arg  Gln  Pro  Thr  Glu
225                      230                     235                      240

Leu  Glu  Val  Ala  Trp  Thr  Pro  Gly  Leu  Ser  Gly  Ile  Tyr  Pro  Leu  Thr
               245                      250                     255

His  Cys  Thr  Leu  Gln  Ala  Val  Leu  Ser  Asp  Asp  Gly  Met  Gly  Ile  Gln
               260                      265                     270

Ala  Gly  Glu  Pro  Asp  Pro  Pro  Glu  Glu  Pro  Leu  Thr  Ser  Gln  Ala  Ser
     275                      280                     285

Val  Pro  Pro  His  Gln  Leu  Arg  Leu  Gly  Ser  Leu  His  Pro  His  Thr  Pro
     290                      295                     300

Tyr  His  Ile  Arg  Val  Ala  Cys  Thr  Ser  Ser  Gln  Gly  Pro  Ser  Ser  Trp
305                      310                     315                      320

Thr  His  Trp  Leu  Pro  Val  Glu  Thr  Pro  Glu  Gly  Val  Pro  Leu  Gly  Pro
               325                      330                     335

Pro  Glu  Asn  Ile  Ser  Ala  Thr  Arg  Asn  Gly  Ser  Gln  Ala  Phe  Val  His
               340                      345                     350

Trp  Gln  Glu  Pro  Arg  Ala  Pro  Leu  Gln  Gly  Thr  Leu  Leu  Gly  Tyr  Arg
          355                      360                     365

Leu  Ala  Tyr  Gln  Gly  Gln  Asp  Thr  Pro  Glu  Val  Leu  Met  Asp  Ile  Gly
     370                      375                     380

Leu  Arg  Gln  Glu  Val  Thr  Leu  Glu  Leu  Gln  Gly  Asp  Gly  Ser  Val  Ser
385                      390                     395                      400

Asn  Leu  Thr  Val  Cys  Val  Ala  Ala  Tyr  Thr  Ala  Ala  Gly  Asp  Gly  Pro
               405                      410                     415

Trp  Ser  Leu  Pro  Val  Pro  Leu  Glu  Ala  Trp  Arg  Pro  Gly  Gln  Ala  Gln
               420                      425                     430

Pro  Val  His  Gln  Leu  Val  Lys  Glu  Pro  Ser  Thr  Pro  Ala  Phe  Ser  Trp
          435                      440                     445

Pro  Trp  Trp  Tyr  Val  Leu  Leu  Gly  Ala  Val  Val  Ala  Ala  Ala  Cys  Val
     450                      455                     460

Leu  Ile  Leu  Ala  Leu  Phe  Leu  Val  His  Arg  Arg  Lys  Lys  Glu  Thr  Arg
465                      470                     475                      480

Tyr  Gly  Glu  Val  Phe  Glu  Pro  Thr  Val  Glu  Arg  Gly  Glu  Leu  Val  Val
               485                      490                     495
```

```
Arg  Tyr  Arg  Val  Arg  Lys  Ser  Tyr  Ser  Arg  Arg  Thr  Thr  Glu  Ala  Thr
               500                       505                      510

Leu  Asn  Ser  Leu  Gly  Ile  Ser  Glu  Glu  Leu  Lys  Glu  Lys  Leu  Arg  Asp
          515                      520                      525

Val  Met  Val  Asp  Arg  His  Lys  Val  Ala  Leu  Gly  Lys  Thr  Leu  Gly  Glu
     530                      535                      540

Gly  Glu  Phe  Gly  Ala  Val  Met  Glu  Gly  Gln  Leu  Asn  Gln  Asp  Asp  Ser
545                      550                      555                      560

Ile  Leu  Lys  Val  Ala  Val  Lys  Thr  Met  Lys  Ile  Ala  Ile  Cys  Thr  Arg
               565                      570                      575

Ser  Glu  Leu  Glu  Asp  Phe  Leu  Ser  Glu  Ala  Val  Cys  Met  Lys  Glu  Phe
               580                      585                      590

Asp  His  Pro  Asn  Val  Met  Arg  Leu  Ile  Gly  Val  Cys  Phe  Gln  Gly  Ser
          595                      600                      605

Glu  Arg  Glu  Ser  Phe  Pro  Ala  Pro  Val  Val  Ile  Leu  Pro  Phe  Met  Lys
          610                      615                      620

His  Gly  Asp  Leu  His  Ser  Phe  Leu  Leu  Tyr  Ser  Arg  Leu  Gly  Asp  Gln
625                      630                      635                      640

Pro  Val  Tyr  Leu  Pro  Thr  Gln  Met  Leu  Val  Lys  Phe  Met  Ala  Asp  Ile
               645                      650                      655

Ala  Ser  Gly  Met  Glu  Tyr  Leu  Ser  Thr  Lys  Arg  Phe  Ile  His  Arg  Asp
               660                      665                      670

Leu  Ala  Ala  Arg  Asn  Cys  Met  Leu  Asn  Glu  Asn  Met  Ser  Val  Cys  Val
          675                      680                      685

Ala  Asp  Phe  Gly  Leu  Ser  Lys  Lys  Ile  Tyr  Asn  Gly  Asp  Tyr  Tyr  Arg
     690                      695                      700

Gln  Gly  Arg  Ile  Ala  Lys  Met  Pro  Val  Lys  Trp  Ile  Ala  Ile  Glu  Ser
705                      710                      715                      720

Leu  Ala  Asp  Arg  Val  Tyr  Thr  Ser  Lys  Ser  Asp  Val  Trp  Ser  Phe  Gly
               725                      730                      735

Val  Thr  Met  Trp  Glu  Ile  Ala  Thr  Arg  Gly  Gln  Thr  Pro  Tyr  Pro  Gly
               740                      745                      750

Val  Glu  Asn  Ser  Glu  Ile  Tyr  Asp  Tyr  Leu  Arg  Gln  Gly  Asn  Arg  Leu
          755                      760                      765

Lys  Gln  Pro  Ala  Asp  Cys  Leu  Asp  Gly  Leu  Tyr  Ala  Leu  Met  Ser  Arg
     770                      775                      780

Cys  Trp  Glu  Leu  Asn  Pro  Gln  Asp  Arg  Pro  Ser  Phe  Thr  Glu  Leu  Arg
785                      790                      795                      800

Glu  Asp  Leu  Glu  Asn  Thr  Leu  Lys  Ala  Leu  Pro  Pro  Ala  Gln  Glu  Pro
               805                      810                      815

Asp  Glu  Ile  Leu  Tyr  Val  Asn  Met  Asp  Glu  Gly  Gly  Gly  Tyr  Pro  Glu
               820                      825                      830

Pro  Pro  Gly  Ala  Ala  Gly  Gly  Ala  Asp  Pro  Pro  Thr  Gln  Pro  Asp  Pro
          835                      840                      845

Lys  Asp  Ser  Cys  Ser  Cys  Leu  Thr  Ala  Ala  Glu  Val  His  Pro  Ala  Gly
     850                      855                      860

Arg  Tyr  Val  Leu  Cys  Pro  Ser  Thr  Thr  Pro  Ser  Pro  Ala  Gln  Pro  Ala
865                      870                      875                      880

Asp  Arg  Gly  Ser  Pro  Ala  Ala  Pro  Gly  Gln  Glu  Asp  Gly  Ala
               885                      890
```

( 2 ) INFORMATION FOR SEQ ID NO:3:

( i ) SEQUENCE CHARACTERISTICS:

-continued (A) LENGTH: 3227 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 159..2813

(xi) SEQUENCE DESCRIPTION: SEQ ID NO:3:

```
GCTGGGCAGA GCCGGTGGCA AGGGCCTCCC CTGCCGCTGT GCCAGGCAGG CAGTGCCAAA      60

TCCGGGGAGC CTGGAGCTGG GGGGAGGGCC GGGGACAGCC CGGCCCTGCC CCCTCCCCCG      120

CTGGGAGCCC AGCAACTTCT GAGGAAAGTT TGGCACCC ATG GCG TGG CGG TGC         173
                                          Met Ala Trp Arg Cys
                                          1               5

CCC AGG ATG GGC AGG GTC CCG CTG GCC TGG TGC TTG GCG CTG TGC GGC       221
Pro Arg Met Gly Arg Val Pro Leu Ala Trp Cys Leu Ala Leu Cys Gly
              10                  15                  20

TGG GCG TGC ATG GCC CCC AGG GGC ACG CAG GCT GAA GAA AGT CCC TTC       269
Trp Ala Cys Met Ala Pro Arg Gly Thr Gln Ala Glu Glu Ser Pro Phe
             25                  30                  35

GTG GGC AAC CCA GGG AAT ATC ACA GGT GCC CGG GGA CTC ACG GGC ACC       317
Val Gly Asn Pro Gly Asn Ile Thr Gly Ala Arg Gly Leu Thr Gly Thr
         40                  45                  50

CTT CGG TGT CAG CTC CAG GTT CAG GGA GAG CCC CCC GAG GTA CAT TGG       365
Leu Arg Cys Gln Leu Gln Val Gln Gly Glu Pro Pro Glu Val His Trp
 55                  60                  65

CTT CGG GAT GGA CAG ATC CTG GAG CTC GCG GAC AGC ACC CAG ACC CAG       413
Leu Arg Asp Gly Gln Ile Leu Glu Leu Ala Asp Ser Thr Gln Thr Gln
 70                  75                  80                  85

GTG CCC CTG GGT GAG GAT GAA CAG GAT GAC TGG ATA GTG GTC AGC CAG       461
Val Pro Leu Gly Glu Asp Glu Gln Asp Asp Trp Ile Val Val Ser Gln
                 90                  95                 100

CTC AGA ATC ACC TCC CTG CAG CTT TCC GAC ACG GGA CAG TAC CAG TGT       509
Leu Arg Ile Thr Ser Leu Gln Leu Ser Asp Thr Gly Gln Tyr Gln Cys
             105                 110                 115

TTG GTG TTT CTG GGA CAT CAG ACC TTC GTG TCC CAG CCT GGC TAT GTT       557
Leu Val Phe Leu Gly His Gln Thr Phe Val Ser Gln Pro Gly Tyr Val
         120                 125                 130

GGG CTG GAG GGC TTG CCT TAC TTC CTG GAG GAG CCC GAA GAC AGG ACT       605
Gly Leu Glu Gly Leu Pro Tyr Phe Leu Glu Glu Pro Glu Asp Arg Thr
 135                 140                 145

GTG GCC GCC AAC ACC CCC TTC AAC CTG AGC TGC CAA GCT CAG GGA CCC       653
Val Ala Ala Asn Thr Pro Phe Asn Leu Ser Cys Gln Ala Gln Gly Pro
150                 155                 160                 165

CCA GAG CCC GTG GAC CTA CTC TGG CTC CAG GAT GCT GTC CCC CTG GCC       701
Pro Glu Pro Val Asp Leu Leu Trp Leu Gln Asp Ala Val Pro Leu Ala
                 170                 175                 180

ACG GCT CCA GGT CAC GGC CCC CAG CGC AGC CTG CAT GTT CCA GGG CTG       749
Thr Ala Pro Gly His Gly Pro Gln Arg Ser Leu His Val Pro Gly Leu
             185                 190                 195

AAC AAG ACA TCC TCT TTC TCC TGC GAA GCC CAT AAC GCC AAG GGG GTC       797
Asn Lys Thr Ser Ser Phe Ser Cys Glu Ala His Asn Ala Lys Gly Val
         200                 205                 210

ACC ACA TCC CGC ACA GCC ACC ATC ACA GTG CTC CCC CAG CAG CCC CGT       845
Thr Thr Ser Arg Thr Ala Thr Ile Thr Val Leu Pro Gln Gln Pro Arg
 215                 220                 225

AAC CTC CAC CTG GTC TCC CGC CAA CCC ACG GAG CTG GAG GTG GCT TGG       893
Asn Leu His Leu Val Ser Arg Gln Pro Thr Glu Leu Glu Val Ala Trp
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 230 |     |     |     |     | 235 |     |     |     |     | 240 |     |     |     |     | 245 |      |
| ACT | CCA | GGC | CTG | AGC | GGC | ATC | TAC | CCC | CTG | ACC | CAC | TGC | ACC | CTG | CAG | 941  |
| Thr | Pro | Gly | Leu | Ser | Gly | Ile | Tyr | Pro | Leu | Thr | His | Cys | Thr | Leu | Gln |      |
|     |     |     |     | 250 |     |     |     |     | 255 |     |     |     |     | 260 |     |      |
| GCT | GTG | CTG | TCA | GAC | GAT | GGG | ATG | GGC | ATC | CAG | GCG | GGA | GAA | CCA | GAC | 989  |
| Ala | Val | Leu | Ser | Asp | Asp | Gly | Met | Gly | Ile | Gln | Ala | Gly | Glu | Pro | Asp |      |
|     |     |     |     | 265 |     |     |     |     | 270 |     |     |     |     | 275 |     |      |
| CCC | CCA | GAG | GAG | CCC | CTC | ACC | TCG | CAA | GCA | TCC | GTG | CCC | CCC | CAT | CAG | 1037 |
| Pro | Pro | Glu | Glu | Pro | Leu | Thr | Ser | Gln | Ala | Ser | Val | Pro | Pro | His | Gln |      |
|     |     |     |     | 280 |     |     |     |     | 285 |     |     |     |     | 290 |     |      |
| CTT | CGG | CTA | GGC | AGC | CTC | CAT | CCT | CAC | ACC | CCT | TAT | CAC | ATC | CGC | GTG | 1085 |
| Leu | Arg | Leu | Gly | Ser | Leu | His | Pro | His | Thr | Pro | Tyr | His | Ile | Arg | Val |      |
|     |     |     |     | 295 |     |     |     |     | 300 |     |     |     |     | 305 |     |      |
| GCA | TGC | ACC | AGC | AGC | CAG | GGC | CCC | TCA | TCC | TGG | ACC | CAC | TGG | CTT | CCT | 1133 |
| Ala | Cys | Thr | Ser | Ser | Gln | Gly | Pro | Ser | Ser | Trp | Thr | His | Trp | Leu | Pro |      |
| 310 |     |     |     |     | 315 |     |     |     |     | 320 |     |     |     |     | 325 |      |
| GTG | GAG | ACG | CCG | GAG | GGA | GTG | CCC | CTG | GGC | CCC | CCT | AAG | AAC | ATT | AGT | 1181 |
| Val | Glu | Thr | Pro | Glu | Gly | Val | Pro | Leu | Gly | Pro | Pro | Lys | Asn | Ile | Ser |      |
|     |     |     |     | 330 |     |     |     |     | 335 |     |     |     |     | 340 |     |      |
| GCT | ACG | CGG | AAT | GGG | AGC | CAG | GCC | TTC | GTG | CAT | TGG | CAA | GAG | CCC | CGG | 1229 |
| Ala | Thr | Arg | Asn | Gly | Ser | Gln | Ala | Phe | Val | His | Trp | Gln | Glu | Pro | Arg |      |
|     |     |     |     | 345 |     |     |     |     | 350 |     |     |     |     | 355 |     |      |
| GCG | CCC | CTG | CAG | GGT | ACC | CTG | TTA | GGG | TAC | CGG | CTG | GCG | TAT | CAA | GGC | 1277 |
| Ala | Pro | Leu | Gln | Gly | Thr | Leu | Leu | Gly | Tyr | Arg | Leu | Ala | Tyr | Gln | Gly |      |
|     |     |     |     | 360 |     |     |     |     | 365 |     |     |     |     | 370 |     |      |
| CAG | GAC | ACC | CCA | GAG | GTG | CTA | ATG | GAC | ATA | GGG | CTA | AGG | CAA | GAG | GTG | 1325 |
| Gln | Asp | Thr | Pro | Glu | Val | Leu | Met | Asp | Ile | Gly | Leu | Arg | Gln | Glu | Val |      |
|     |     |     |     | 375 |     |     |     |     | 380 |     |     |     |     | 385 |     |      |
| ACC | CTG | GAG | CTG | CAG | GGG | GAC | GGG | TCT | GTG | TCC | AAT | CTG | ACA | GTG | TGT | 1373 |
| Thr | Leu | Glu | Leu | Gln | Gly | Asp | Gly | Ser | Val | Ser | Asn | Leu | Thr | Val | Cys |      |
| 390 |     |     |     |     | 395 |     |     |     |     | 400 |     |     |     |     | 405 |      |
| GTG | GCA | GCC | TAC | ACT | GCT | GCT | GGG | GAT | GGA | CCC | TGG | AGC | CTC | CCA | GTA | 1421 |
| Val | Ala | Ala | Tyr | Thr | Ala | Ala | Gly | Asp | Gly | Pro | Trp | Ser | Leu | Pro | Val |      |
|     |     |     |     | 410 |     |     |     |     | 415 |     |     |     |     | 420 |     |      |
| CCC | CTG | GAG | GCC | TGG | CGC | CCA | GTG | AAG | GAA | CCT | TCA | ACT | CCT | GCC | TTC | 1469 |
| Pro | Leu | Glu | Ala | Trp | Arg | Pro | Val | Lys | Glu | Pro | Ser | Thr | Pro | Ala | Phe |      |
|     |     |     |     | 425 |     |     |     |     | 430 |     |     |     |     | 435 |     |      |
| TCG | TGG | CCC | TGG | TGG | TAT | GTA | CTG | CTA | GGA | GCA | GTC | GTG | GCC | GCT | GCC | 1517 |
| Ser | Trp | Pro | Trp | Trp | Tyr | Val | Leu | Leu | Gly | Ala | Val | Val | Ala | Ala | Ala |      |
|     |     |     |     | 440 |     |     |     |     | 445 |     |     |     |     | 450 |     |      |
| TGT | GTC | CTC | ATC | TTG | GCT | CTC | TTC | CTT | GTC | CAC | CGG | CGA | AAG | AAG | GAG | 1565 |
| Cys | Val | Leu | Ile | Leu | Ala | Leu | Phe | Leu | Val | His | Arg | Arg | Lys | Lys | Glu |      |
|     |     |     |     | 455 |     |     |     |     | 460 |     |     |     |     | 465 |     |      |
| ACC | CGT | TAT | GGA | GAA | GTG | TTT | GAA | CCA | ACA | GTG | GAA | AGA | GGT | GAA | CTG | 1613 |
| Thr | Arg | Tyr | Gly | Glu | Val | Phe | Glu | Pro | Thr | Val | Glu | Arg | Gly | Glu | Leu |      |
| 470 |     |     |     |     | 475 |     |     |     |     | 480 |     |     |     |     | 485 |      |
| GTA | GTC | AGG | TAC | CGC | GTG | CGC | AAG | TCC | TAC | AGT | CGT | CGG | ACC | ACT | GAA | 1661 |
| Val | Val | Arg | Tyr | Arg | Val | Arg | Lys | Ser | Tyr | Ser | Arg | Arg | Thr | Thr | Glu |      |
|     |     |     |     | 490 |     |     |     |     | 495 |     |     |     |     | 500 |     |      |
| GCT | ACC | TTG | AAC | AGC | CTG | GGC | ATC | AGT | GAA | GAG | CTG | AAG | GAG | AAG | CTG | 1709 |
| Ala | Thr | Leu | Asn | Ser | Leu | Gly | Ile | Ser | Glu | Glu | Leu | Lys | Glu | Lys | Leu |      |
|     |     |     |     | 505 |     |     |     |     | 510 |     |     |     |     | 515 |     |      |
| CGG | GAT | GTG | ATG | GTG | GAC | CGG | CAC | AAG | GTG | GCC | CTG | GGG | AAG | ACT | CTG | 1757 |
| Arg | Asp | Val | Met | Val | Asp | Arg | His | Lys | Val | Ala | Leu | Gly | Lys | Thr | Leu |      |
|     |     |     |     | 520 |     |     |     |     | 525 |     |     |     |     | 530 |     |      |
| GGA | GAG | GGA | GAG | TTT | GGA | GCT | GTG | ATG | GAA | GGC | CAG | CTC | AAC | CAG | GAC | 1805 |
| Gly | Glu | Gly | Glu | Phe | Gly | Ala | Val | Met | Glu | Gly | Gln | Leu | Asn | Gln | Asp |      |
|     |     |     |     | 535 |     |     |     |     | 540 |     |     |     |     | 545 |     |      |
| GAC | TCC | ATC | CTC | AAG | GTG | GCT | GTG | AAG | ACG | ATG | AAG | ATT | GCC | ATC | TGC | 1853 |

```
Asp Ser Ile Leu Lys Val Ala Val Lys Thr Met Lys Ile Ala Ile Cys
550             555             560             565

ACG AGG TCA GAG CTG GAG GAT TTC CTG AGT GAA GCG GTC TGC ATG AAG    1901
Thr Arg Ser Glu Leu Glu Asp Phe Leu Ser Glu Ala Val Cys Met Lys
            570             575             580

GAA TTT GAC CAT CCC AAC GTC ATG AGG CTC ATT GGT GTC TGT TTC CAG    1949
Glu Phe Asp His Pro Asn Val Met Arg Leu Ile Gly Val Cys Phe Gln
        585             590             595

GGT TCT GAA CGA GAG AGC TTC CCA GCA CCT GTG GTC ATC TTA CCT TTC    1997
Gly Ser Glu Arg Glu Ser Phe Pro Ala Pro Val Val Ile Leu Pro Phe
        600             605             610

ATG AAA CAT GGA GAC CTA CAC AGC TTC CTC CTC TAT TCC CGG CTC GGG    2045
Met Lys His Gly Asp Leu His Ser Phe Leu Leu Tyr Ser Arg Leu Gly
615             620             625

GAC CAG CCA GTG TAC CTG CCC ACT CAG ATG CTA GTG AAG TTC ATG GCA    2093
Asp Gln Pro Val Tyr Leu Pro Thr Gln Met Leu Val Lys Phe Met Ala
630             635             640             645

GAC ATC GCC AGT GGC ATG GAG TAT CTG AGT ACC AAG AGA TTC ATA CAC    2141
Asp Ile Ala Ser Gly Met Glu Tyr Leu Ser Thr Lys Arg Phe Ile His
            650             655             660

CGG GAC CTG GCG GCC AGG AAC TGC ATG CTG AAT GAG AAC ATG TCC GTG    2189
Arg Asp Leu Ala Ala Arg Asn Cys Met Leu Asn Glu Asn Met Ser Val
        665             670             675

TGT GTG GCG GAC TTC GGG CTC TCC AAG AAG ATC TAC AAT GGG GAC TAC    2237
Cys Val Ala Asp Phe Gly Leu Ser Lys Lys Ile Tyr Asn Gly Asp Tyr
        680             685             690

TAC CGC CAG GGA CGT ATC GCC AAG ATG CCA GTC AAG TGG ATT GCC ATT    2285
Tyr Arg Gln Gly Arg Ile Ala Lys Met Pro Val Lys Trp Ile Ala Ile
695             700             705

GAG AGT CTA GCT GAC CGT GTC TAC ACC AGC AAG AGC GAT GTG TGG TCC    2333
Glu Ser Leu Ala Asp Arg Val Tyr Thr Ser Lys Ser Asp Val Trp Ser
710             715             720             725

TTC GGG GTG ACA ATG TGG GAG ATT GCC ACA AGA GGC CAA ACC CCA TAT    2381
Phe Gly Val Thr Met Trp Glu Ile Ala Thr Arg Gly Gln Thr Pro Tyr
            730             735             740

CCG GGC GTG GAG AAC AGC GAG ATT TAT GAC TAT CTG CGC CAG GGA AAT    2429
Pro Gly Val Glu Asn Ser Glu Ile Tyr Asp Tyr Leu Arg Gln Gly Asn
            745             750             755

CGC CTG AAG CAG CCT GCG GAC TGT CTG GAT GGA CTG TAT GCC TTG ATG    2477
Arg Leu Lys Gln Pro Ala Asp Cys Leu Asp Gly Leu Tyr Ala Leu Met
        760             765             770

TCG CGG TGC TGG GAG CTA AAT CCC CAG GAC CGG CCA AGT TTT ACA GAG    2525
Ser Arg Cys Trp Glu Leu Asn Pro Gln Asp Arg Pro Ser Phe Thr Glu
        775             780             785

CTG CGG GAA GAT TTG GAG AAC ACA CTG AAG GCC TTG CCT CCT GCC CAG    2573
Leu Arg Glu Asp Leu Glu Asn Thr Leu Lys Ala Leu Pro Pro Ala Gln
790             795             800             805

GAG CCT GAC GAA ATC CTC TAT GTC AAC ATG GAT GAG GGT GGA GGT TAT    2621
Glu Pro Asp Glu Ile Leu Tyr Val Asn Met Asp Glu Gly Gly Gly Tyr
            810             815             820

CCT GAA CCC CCT GGA GCT GCA GGA GGA GCT GAC CCC CCA ACC CAG CCA    2669
Pro Glu Pro Pro Gly Ala Ala Gly Gly Ala Asp Pro Pro Thr Gln Pro
        825             830             835

GAC CCT AAG GAT TCC TGT AGC TGC CTC ACT GCG GCT GAG GTC CAT CCT    2717
Asp Pro Lys Asp Ser Cys Ser Cys Leu Thr Ala Ala Glu Val His Pro
        840             845             850

GCT GGA CGC TAT GTC CTC TGC CCT TCC ACA ACC CCT AGC CCC GCT CAG    2765
Ala Gly Arg Tyr Val Leu Cys Pro Ser Thr Thr Pro Ser Pro Ala Gln
855             860             865
```

| CCT | GCT | GAT | AGG | GGC | TCC | CCA | GCA | GCC | CCA | GGG | CAG | GAG | GAT | GGT | GCC | 2813 |
|-----|-----|-----|-----|-----|-----|-----|-----|-----|-----|-----|-----|-----|-----|-----|-----|------|
| Pro | Ala | Asp | Arg | Gly | Ser | Pro | Ala | Ala | Pro | Gly | Gln | Glu | Asp | Gly | Ala |  |
| 870 |  |  |  |  | 875 |  |  |  | 880 |  |  |  |  |  | 885 |  |

| TGAGACAACC | CTCCACCTGG | TACTCCCTCT | CAGGATCCAA | GCTAAGCACT | GCCACTGGGG | 2873 |
| AAAACTCCAC | CTTCCCACTT | TCCCACCCCA | CGCCTTATCC | CCACTTGCAG | CCCTGTCTTC | 2933 |
| CTACCTATCC | CACCTCCATC | CCAGACAGGT | CCCTCCCCTT | CTCTGTGCAG | TAGCATCACC | 2993 |
| TTGAAAGCAG | TAGCATCACC | ATCTGTAAAA | GGAAGGGGTT | GGATTGCAAT | ATCTGAAGCC | 3053 |
| CTCCCAGGTG | TTAACATTCC | AAGACTCTAG | AGTCCAAGGT | TTAAAGAGTC | TAGATTCAAA | 3113 |
| GGTTCTAGGT | TTCAAAGATG | CTGTGAGTCT | TTGGTTCTAA | GGACCTGAAA | TTCCAAAGTC | 3173 |
| TCTAATTCTA | TTAAAGTGCT | AAGGTTCTAA | AAAAAAAAAA | AAAAAAAAA | AAAA | 3227 |

( 2 ) INFORMATION FOR SEQ ID NO:4:

( i ) SEQUENCE CHARACTERISTICS:
        ( A ) LENGTH: 885 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Trp | Arg | Cys | Pro | Arg | Met | Gly | Arg | Val | Pro | Leu | Ala | Trp | Cys |
|-----|-----|-----|-----|-----|-----|-----|-----|-----|-----|-----|-----|-----|-----|-----|-----|
| 1 |  |  |  | 5 |  |  |  |  | 10 |  |  |  |  |  | 15 |
| Leu | Ala | Leu | Cys | Gly | Trp | Ala | Cys | Met | Ala | Pro | Arg | Gly | Thr | Gln | Ala |
|  |  |  | 20 |  |  |  |  | 25 |  |  |  |  |  | 30 |  |
| Glu | Glu | Ser | Pro | Phe | Val | Gly | Asn | Pro | Gly | Asn | Ile | Thr | Gly | Ala | Arg |
|  |  | 35 |  |  |  |  | 40 |  |  |  |  | 45 |  |  |  |
| Gly | Leu | Thr | Gly | Thr | Leu | Arg | Cys | Gln | Leu | Gln | Val | Gln | Gly | Glu | Pro |
|  | 50 |  |  |  |  | 55 |  |  |  |  | 60 |  |  |  |  |
| Pro | Glu | Val | His | Trp | Leu | Arg | Asp | Gly | Gln | Ile | Leu | Glu | Leu | Ala | Asp |
| 65 |  |  |  |  | 70 |  |  |  |  | 75 |  |  |  |  | 80 |
| Ser | Thr | Gln | Thr | Gln | Val | Pro | Leu | Gly | Glu | Asp | Glu | Gln | Asp | Asp | Trp |
|  |  |  |  | 85 |  |  |  |  | 90 |  |  |  |  | 95 |  |
| Ile | Val | Val | Ser | Gln | Leu | Arg | Ile | Thr | Ser | Leu | Gln | Leu | Ser | Asp | Thr |
|  |  |  | 100 |  |  |  |  | 105 |  |  |  |  | 110 |  |  |
| Gly | Gln | Tyr | Gln | Cys | Leu | Val | Phe | Leu | Gly | His | Gln | Thr | Phe | Val | Ser |
|  |  | 115 |  |  |  |  | 120 |  |  |  |  | 125 |  |  |  |
| Gln | Pro | Gly | Tyr | Val | Gly | Leu | Glu | Gly | Leu | Pro | Tyr | Phe | Leu | Glu | Glu |
|  | 130 |  |  |  |  | 135 |  |  |  |  | 140 |  |  |  |  |
| Pro | Glu | Asp | Arg | Thr | Val | Ala | Ala | Asn | Thr | Pro | Phe | Asn | Leu | Ser | Cys |
| 145 |  |  |  |  | 150 |  |  |  |  | 155 |  |  |  |  | 160 |
| Gln | Ala | Gln | Gly | Pro | Pro | Glu | Pro | Val | Asp | Leu | Leu | Trp | Leu | Gln | Asp |
|  |  |  |  | 165 |  |  |  |  | 170 |  |  |  |  | 175 |  |
| Ala | Val | Pro | Leu | Ala | Thr | Ala | Pro | Gly | His | Gly | Pro | Gln | Arg | Ser | Leu |
|  |  |  | 180 |  |  |  |  | 185 |  |  |  |  | 190 |  |  |
| His | Val | Pro | Gly | Leu | Asn | Lys | Thr | Ser | Ser | Phe | Ser | Cys | Glu | Ala | His |
|  |  | 195 |  |  |  |  | 200 |  |  |  |  | 205 |  |  |  |
| Asn | Ala | Lys | Gly | Val | Thr | Thr | Ser | Arg | Thr | Ala | Thr | Ile | Thr | Val | Leu |
|  | 210 |  |  |  |  | 215 |  |  |  |  | 220 |  |  |  |  |
| Pro | Gln | Gln | Pro | Arg | Asn | Leu | His | Leu | Val | Ser | Arg | Gln | Pro | Thr | Glu |
| 225 |  |  |  |  | 230 |  |  |  |  | 235 |  |  |  |  | 240 |
| Leu | Glu | Val | Ala | Trp | Thr | Pro | Gly | Leu | Ser | Gly | Ile | Tyr | Pro | Leu | Thr |
|  |  |  |  | 245 |  |  |  |  | 250 |  |  |  |  | 255 |  |
| His | Cys | Thr | Leu | Gln | Ala | Val | Leu | Ser | Asp | Asp | Gly | Met | Gly | Ile | Gln |

-continued

|     |     |     | 260 |     |     |     | 265 |     |     |     | 270 |     |     |     |
|-----|-----|-----|-----|-----|-----|-----|-----|-----|-----|-----|-----|-----|-----|-----|
| Ala | Gly | Glu | Pro | Asp | Pro | Pro | Glu | Pro | Leu | Thr | Ser | Gln | Ala | Ser |
|     |     | 275 |     |     |     | 280 |     |     |     | 285 |     |     |     |     |
| Val | Pro | Pro | His | Gln | Leu | Arg | Leu | Gly | Ser | Leu | His | Pro | His | Thr | Pro |
|     | 290 |     |     |     |     | 295 |     |     |     |     | 300 |     |     |     |
| Tyr | His | Ile | Arg | Val | Ala | Cys | Thr | Ser | Ser | Gln | Gly | Pro | Ser | Ser | Trp |
| 305 |     |     |     |     | 310 |     |     |     |     | 315 |     |     |     |     | 320 |
| Thr | His | Trp | Leu | Pro | Val | Glu | Thr | Pro | Glu | Gly | Val | Pro | Leu | Gly | Pro |
|     |     |     |     | 325 |     |     |     |     | 330 |     |     |     |     | 335 |     |
| Pro | Lys | Asn | Ile | Ser | Ala | Thr | Arg | Asn | Gly | Ser | Gln | Ala | Phe | Val | His |
|     |     |     | 340 |     |     |     |     | 345 |     |     |     |     | 350 |     |     |
| Trp | Gln | Glu | Pro | Arg | Ala | Pro | Leu | Gln | Gly | Thr | Leu | Leu | Gly | Tyr | Arg |
|     |     | 355 |     |     |     |     | 360 |     |     |     |     | 365 |     |     |     |
| Leu | Ala | Tyr | Gln | Gly | Gln | Asp | Thr | Pro | Glu | Val | Leu | Met | Asp | Ile | Gly |
|     | 370 |     |     |     |     | 375 |     |     |     |     | 380 |     |     |     |     |
| Leu | Arg | Gln | Glu | Val | Thr | Leu | Glu | Leu | Gln | Gly | Asp | Gly | Ser | Val | Ser |
| 385 |     |     |     |     | 390 |     |     |     |     | 395 |     |     |     |     | 400 |
| Asn | Leu | Thr | Val | Cys | Val | Ala | Ala | Tyr | Thr | Ala | Ala | Gly | Asp | Gly | Pro |
|     |     |     |     | 405 |     |     |     |     | 410 |     |     |     |     | 415 |     |
| Trp | Ser | Leu | Pro | Val | Pro | Leu | Glu | Ala | Trp | Arg | Pro | Val | Lys | Glu | Pro |
|     |     |     | 420 |     |     |     |     | 425 |     |     |     |     | 430 |     |     |
| Ser | Thr | Pro | Ala | Phe | Ser | Trp | Pro | Trp | Trp | Tyr | Val | Leu | Leu | Gly | Ala |
|     |     | 435 |     |     |     |     | 440 |     |     |     |     | 445 |     |     |     |
| Val | Val | Ala | Ala | Ala | Cys | Val | Leu | Ile | Leu | Ala | Leu | Phe | Leu | Val | His |
|     | 450 |     |     |     |     | 455 |     |     |     |     | 460 |     |     |     |     |
| Arg | Arg | Lys | Lys | Glu | Thr | Arg | Tyr | Gly | Glu | Val | Phe | Glu | Pro | Thr | Val |
| 465 |     |     |     |     | 470 |     |     |     |     | 475 |     |     |     |     | 480 |
| Glu | Arg | Gly | Glu | Leu | Val | Val | Arg | Tyr | Arg | Val | Arg | Lys | Ser | Tyr | Ser |
|     |     |     |     | 485 |     |     |     |     | 490 |     |     |     |     | 495 |     |
| Arg | Arg | Thr | Thr | Glu | Ala | Thr | Leu | Asn | Ser | Leu | Gly | Ile | Ser | Glu | Glu |
|     |     |     | 500 |     |     |     |     | 505 |     |     |     |     | 510 |     |     |
| Leu | Lys | Glu | Lys | Leu | Arg | Asp | Val | Met | Val | Asp | Arg | His | Lys | Val | Ala |
|     |     | 515 |     |     |     |     | 520 |     |     |     |     | 525 |     |     |     |
| Leu | Gly | Lys | Thr | Leu | Gly | Glu | Gly | Glu | Phe | Gly | Ala | Val | Met | Glu | Gly |
|     | 530 |     |     |     |     | 535 |     |     |     |     | 540 |     |     |     |     |
| Gln | Leu | Asn | Gln | Asp | Asp | Ser | Ile | Leu | Lys | Val | Ala | Val | Lys | Thr | Met |
| 545 |     |     |     |     | 550 |     |     |     |     | 555 |     |     |     |     | 560 |
| Lys | Ile | Ala | Ile | Cys | Thr | Arg | Ser | Glu | Leu | Glu | Asp | Phe | Leu | Ser | Glu |
|     |     |     |     | 565 |     |     |     |     | 570 |     |     |     |     | 575 |     |
| Ala | Val | Cys | Met | Lys | Glu | Phe | Asp | His | Pro | Asn | Val | Met | Arg | Leu | Ile |
|     |     |     | 580 |     |     |     |     | 585 |     |     |     |     | 590 |     |     |
| Gly | Val | Cys | Phe | Gln | Gly | Ser | Glu | Arg | Glu | Ser | Phe | Pro | Ala | Pro | Val |
|     |     |     | 595 |     |     |     |     | 600 |     |     |     |     | 605 |     |     |
| Val | Ile | Leu | Pro | Phe | Met | Lys | His | Gly | Asp | Leu | His | Ser | Phe | Leu | Leu |
|     | 610 |     |     |     |     | 615 |     |     |     |     | 620 |     |     |     |     |
| Tyr | Ser | Arg | Leu | Gly | Asp | Gln | Pro | Val | Tyr | Leu | Pro | Thr | Gln | Met | Leu |
| 625 |     |     |     |     | 630 |     |     |     |     | 635 |     |     |     |     | 640 |
| Val | Lys | Phe | Met | Ala | Asp | Ile | Ala | Ser | Gly | Met | Glu | Tyr | Leu | Ser | Thr |
|     |     |     |     | 645 |     |     |     |     | 650 |     |     |     |     | 655 |     |
| Lys | Arg | Phe | Ile | His | Arg | Asp | Leu | Ala | Ala | Arg | Asn | Cys | Met | Leu | Asn |
|     |     |     | 660 |     |     |     |     | 665 |     |     |     |     | 670 |     |     |
| Glu | Asn | Met | Ser | Val | Cys | Val | Ala | Asp | Phe | Gly | Leu | Ser | Lys | Lys | Ile |
|     |     | 675 |     |     |     |     | 680 |     |     |     |     | 685 |     |     |     |

| | | | | | | | | | | | | | | |
|---|---|---|---|---|---|---|---|---|---|---|---|---|---|---|
| Tyr | Asn | Gly | Asp | Tyr | Tyr | Arg | Gln | Gly | Arg | Ile | Ala | Lys | Met | Pro | Val |
| | 690 | | | | 695 | | | | | 700 | | | | |
| Lys | Trp | Ile | Ala | Ile | Glu | Ser | Leu | Ala | Asp | Arg | Val | Tyr | Thr | Ser | Lys |
| 705 | | | | | 710 | | | | | 715 | | | | | 720 |
| Ser | Asp | Val | Trp | Ser | Phe | Gly | Val | Thr | Met | Trp | Glu | Ile | Ala | Thr | Arg |
| | | | | 725 | | | | | 730 | | | | | 735 | |
| Gly | Gln | Thr | Pro | Tyr | Pro | Gly | Val | Glu | Asn | Ser | Glu | Ile | Tyr | Asp | Tyr |
| | | | 740 | | | | | 745 | | | | | 750 | | |
| Leu | Arg | Gln | Gly | Asn | Arg | Leu | Lys | Gln | Pro | Ala | Asp | Cys | Leu | Asp | Gly |
| | | 755 | | | | | 760 | | | | | 765 | | | |
| Leu | Tyr | Ala | Leu | Met | Ser | Arg | Cys | Trp | Glu | Leu | Asn | Pro | Gln | Asp | Arg |
| | 770 | | | | | 775 | | | | | 780 | | | | |
| Pro | Ser | Phe | Thr | Glu | Leu | Arg | Glu | Asp | Leu | Glu | Asn | Thr | Leu | Lys | Ala |
| 785 | | | | | 790 | | | | | 795 | | | | | 800 |
| Leu | Pro | Pro | Ala | Gln | Glu | Pro | Asp | Glu | Ile | Leu | Tyr | Val | Asn | Met | Asp |
| | | | | 805 | | | | | 810 | | | | | 815 | |
| Glu | Gly | Gly | Gly | Tyr | Pro | Glu | Pro | Pro | Gly | Ala | Ala | Gly | Gly | Ala | Asp |
| | | | 820 | | | | | 825 | | | | | 830 | | |
| Pro | Pro | Thr | Gln | Pro | Asp | Pro | Lys | Asp | Ser | Cys | Ser | Cys | Leu | Thr | Ala |
| | | 835 | | | | | 840 | | | | | 845 | | | |
| Ala | Glu | Val | His | Pro | Ala | Gly | Arg | Tyr | Val | Leu | Cys | Pro | Ser | Thr | Thr |
| | 850 | | | | | 855 | | | | | 860 | | | | |
| Pro | Ser | Pro | Ala | Gln | Pro | Ala | Asp | Arg | Gly | Ser | Pro | Ala | Ala | Pro | Gly |
| 865 | | | | | 870 | | | | | 875 | | | | | 880 |
| Gln | Glu | Asp | Gly | Ala | | | | | | | | | | | |
| | | | | 885 | | | | | | | | | | | |

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGAGCAATGA TCTTGATCTT C           21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CCTTCCTGGG CATGGAGTCC T           21

AXL ONCOGENE

This invention was made with Government support under grant number RO1 CA49240-01 from the National Cancer Institute. The Government may have certain rights to this invention. This is a continuation of copending application Ser. No. 07/718,572, filed on Jun. 24, 1991, now abandoned.

FIELD OF THE INVENTION

The present invention relates to oncogenes in general, and particularly relates to an oncogene which codes for a receptor having tyrosine kinase activity.

BACKGROUND OF THE INVENTION

Receptor tyrosine kinases represent a class of proteins that transduce signals from the extracellular milieu into the cytoplasm by binding peptide growth factors. These growth factors and their cognate receptors are involved in regulating cellular growth and differentiation. Alteration of either growth factors or their receptors can result in neoplastic transformation and altered development. See M. Cross and T. Dexter, Cell 64:271 (1991). There are several mechanisms by which growth factor receptors can be rendered transforming. Retroviral transduction of proto-oncogenes can result in truncation and mutation of the normal version of the gene. This has been shown for the EGF receptor (v-erbB) (J. Downward et al., Nature 307:521 (1984)), CSF-1 receptor (v-fms) (C. Sherr, Blood 75:1 (1990)) and ros (v-ros) (H. Matsushime et al., Mol. Cell. Biol. 6:3000 (1986)). Overexpression of an otherwise normal receptor, with or without the concomitant application of ligand, can also result in neoplastic transformation as shown for the IGF-1R (M. Kaleko et al., Mol. Cell. Biol. 10:464 (1990)), EGFR (P. Di Fiore et al., Cell 51:1063 (1987); T. Velu et al., Science 238:1408 (1987)), CSF-1R (M. Roussel et al., Nature (London) 325:549 (1987)), eph (Y. Maru et al., Oncogene 5:445 (1990)) and neu (P. Di Fiore et al., Science 237:178 (1987)). Furthermore, structural rearrangement, as seen with ret, trk, and met, may also activate the transforming capacity of receptor kinases. See M. Grieco et al., Cell 60:557 (1990); D. Martin-Zanca et al., Nature (London) 319:743 (1986); M. Park et al., Cell 45:895 (1986).

In addition to the transforming activity of altered or overexpressed receptor tyrosine kinases, studies have demonstrated that the normal cellular homologues of these receptors function to regulate cell growth and differentiation. Examples include the trk receptor kinase originally isolated by genomic transfection of human colon carcinoma DNA into NIH/3T3 cells. D. Martin-Zanca et al., supra. Although trk is not generally involved in colon cancer, recent work has demonstrated that this gene encodes a subunit of the nerve growth factor receptor which plays a critical role in neural development. See D. Kaplan et al., Science 252:554 (1991); R. Klein et al., Cell 65:189 (1991). Furthermore, the met proto-oncogene, originally isolated by transfection of 3T3 cells with genomic DNA from a tumorigenic human osteogenic sarcoma cell line MNNG-HOS (C. Cooper et al., Nature (London) 311:29 (1984)), has been demonstrated to be the cell-surface receptor for hepatocyte growth factor, a potential growth factor for a broad spectrum of cell types as well as a mediator of liver regeneration. D. Bottaro et al., Science 251:802 (1991). In addition, the CSF-1 receptor mediates the pleiotrophic effects of its cognate ligand, colony-stimulating factor-1 (CSF-1). Together these two molecules stimulate the proliferation and differentiation of cells of the macrophage lineage. C. Sherr, supra.

One oncogene which has been of considerable interest is neu (also known as "her2"). Methods for the detection of neu gene expression and products are disclosed in PCT Application WO 89/10412. Methods of treating tumor cells by inhibiting the function of a growth factor receptor such as HER2 receptor are disclosed in PCT Application WO 89/06692. Methods of detecting point mutations in the neu gene are disclosed in U.S. Pat. No. 4,935,341. Genes in this family are thought to be activated by the alteration of a single nucleotide in the normal cellular DNA sequence (the protooncogene), resulting in activation of the oncogene. This point mutation was initially seen in a rat neuroblastoma induced by transplacental exposure to a carcinogen.

In an effort to determine genes involved in the progression of chronic myelogenous leukemia (CML) to acute phase leukemia, we previously reported the identification of a transforming gene in the DNAs of two patients with CML. See E. Liu et al., Proc. Natl Acad. Sci. U.S.A. 85:1952 (1988). We term this gene axl (anexelekto, anexelekto=axl, Greek for "uncontrolled"). The present invention is based upon our ongoing interest in investigating this gene.

SUMMARY OF THE INVENTION

Described herein is the molecular cloning and characterization of the axl gene. These data show that axl is a receptor tyrosine kinase with a structure unique amongst tyrosine kinases. Our data indicate that the axl protein has tyrosine kinase activity and is capable of transforming NIH/3T3 cells. Furthermore, axl's transforming capacity results from overexpression of axl mRNA rather than structural mutation.

In accordance with the foregoing, disclosed is an isolated DNA sequence encoding a mammalian axl receptor which exhibits axl oncogene activity. More particularly, such DNA sequences are DNA sequences selected from the group consisting of: (a) isolated DNA which encodes a human axl oncogene; (b) isolated DNA which hybridizes to isolated DNA of (a) above and which encodes an axl receptor; and (c) isolated DNA differing from the isolated DNAs of (a) and (b) above in nucleotide sequence due to the degeneracy of the genetic code, and which encodes an axl receptor. Recombinant DNA comprising vector DNA and a DNA as described above, along with host cells containing such recombinant DNA and capable of expressing the same, are also disclosed.

Also disclosed is an isolated and purified axl receptor selected from the group consisting of mammalian axl receptor proteins and soluble extracellular fragments thereof having axl receptor binding activity. More particularly, such receptors are axl receptors coded for by a DNA sequence selected from the group consisting of: (a) DNA which encodes a human axl oncogene; (b) DNA which hybridizes to isolated DNA of (a) above and which encodes an axl receptor; (c) DNA differing from the DNAs of (a) and (b) above in nucleotide sequence due to the degeneracy of the genetic code, and which encodes an axl receptor; and (d) DNA which encodes a soluble extracellular fragment of an axl receptor protein encoded by a DNA of (a), (b), or (c) above, which fragment has axl receptor binding activity.

Also disclosed are soluble mammalian axl receptor which exhibits axl receptor binding activity. Such receptors may comprise a mammalian axl receptor having a deleted transmembrane region, or the extracellular portion of a mammalian axl receptor protein.

Also disclosed are recombinant DNA constructs coding for chimeric proteins, along with the coded-for chimeric proteins. The chimerics protein comprise an an axl receptor extracellular portion having axl receptor binding activity operatively associated an effector portion capable of generating a detectable signal upon binding of a ligand to said axl receptor extracellular portion.

Also disclosed herein are antibodies, such as monoclonal antibodies, which specifically binds to the axl receptor, along with hybridomas for making such monoclonal antibodies.

Also disclosed is an assay for detecting a tumor. The assay comprises the steps of, first, contacting cells to antibodies capable of specifically binding the extracellular domain of the axl receptor, and then determining the extend of binding of said antibodies to said cells.

DETAILED DESCRIPTION OF THE INVENTION

The term "oncogene", as used herein, refers to a genetic sequence whose expression within a cell induces that cell to become converted from a normal cell into a tumor cell.

A. Genetic Engineering Techniques

The production of cloned genes, recombinant DNA, vectors, transformed host cells, proteins and protein fragments by genetic engineering is well known. See, e.g., U.S. Pat. No. 4,761,371, to Bell et al. at Col. 6 line 3 to Col. 9 line 65; U.S. Pat. No. 4,877,729, to Clark et al. at Col. 4 line 38 to Col. 7 line 6; U.S. Pat. No. 4,912,038, to Schilling at Col. 3 line 26 to Col. 14 line 12; and U.S. Pat. No. 4,879,224, to Wallner at Col. 6 line 8 to Col. 8 line 59.

A vector is a replicable DNA construct. Vectors are used herein either to amplify DNA encoding axl and/or to express axl. An expression vector is a replicable DNA construct in which an axl oncogene is operably linked to suitable control sequences capable of effecting the expression of axl in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing an axl oncogene constructed using recombinant DNA techniques. Transformed host cells ordinarily express axl, but host cells transformed for purposes of cloning or amplifying axl oncogene DNA need not express axl.

Suitable host cells include prokaryote, yeast or higher eukaryotic cells such as mammalian cells and insect cells. Cells derived from multicellular organisms are a particularly suitable host for synthesis of the axl oncogene receptor by recombinant means, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the axl oncogene to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the axl oncogene. Examples of suitable selectable markers are dihydrofolate reductase (DHFR) or thymidine kinase. This method is further described in U.S. Pat. No. 4,399,216 (Applicant specifically intends that the disclosure of all patent references cited herein be incorporated herein by reference).

Other methods suitable for adaptation to the expression of an axl oncogene in recombinant vertebrate cell culture include those described in M-J. Gething et al., *Nature* 293, 620 (1981); N. Mantei et al., *Nature* 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236, to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the betalactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the axl oncogene, i.e., they are positioned so as to promote transcription of axl oncogene messenger RNA from the DNA.

Eukaryotic microbes such as yeast cultures may also be transformed with axl oncogene vectors. see, e.g., U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, an axl oncogene, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

B. Axl Oncogenes

Axl oncogenes of the present invention include those coding for proteins homologous to, and having essentially the same biological properties as, the human axl oncogenes disclosed herein, and particularly the human axl oncogenes disclosed herein as SEQ ID NO: 1 and SEQ ID NO: 3. This definition is intended to encompass natural allelic variations in the axl oncogene. Cloned genes of the present invention can be of any species of origin, including mouse, rat, rabbit, cat, porcine, and human, but are preferably of mammalian origin. Thus, DNA sequences which hybridize to DNA which encodes human axl and which code on expression for an axl receptor protein are also an aspect of this invention. Conditions which will permit other DNA sequences which code on expression for an axl receptor protein to hybridize to the DNA sequence of the human axl oncogenes disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5x Denhardt's solution, 0.5% SDS and 1x SSPE at 37° C.; conditions represented by a wash stringency of 40–45% Formamide with 5x Denhardt's solution, 0.5% SDS, and 1x SSPE at 42° C.; and conditions represented by a wash stringency of 50% Formamide with 5x Denhardt's solution, 0.5% SDS and 1x SSPE at 42° C., respectively, to DNA encoding the axl oncogene disclosed herein in a standard hybridization assay. See J. Sambrook et al., Molecular Cloning, A Laboratory Manual (2d Ed. 1989)(Cold Spring Harbor Laboratory)). In general, sequences which code for axl receptor protein and hybridize to the axl oncogenes disclosed herein will be at least 75% homologous, 85% homologous, and even 95% homologous or more with the sequence of the human axl oncogenes disclosed herein. Further, DNA sequences which code for axl receptor proteins, or sequences which code for a receptor protein coded for by a sequence which hybridizes to the DNA sequences which code for human axl oncogenes disclosed herein, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006, to Toole et al. at Col. 2, Table 1.

Knowledge of the axl nucleotide sequence as disclosed herein can be used to generate hybridization probes which specifically bind to the axl gene to determine the presence of axl gene amplification or overexpression. The hybridization probes may be cDNA fragments or oligonucleotides, and may be labelled with a detectable group as discussed hereinbelow. Pairs of probes which will serve as PCR primers for the axl oncogene or a portion thereof may be used in accordance with the process described in U.S. Pat. Nos. 4,683,202, and 4,683,195.

C. Axl Receptors and Proteins

As noted above, the present invention provides isolated and purified axl receptors, such as mammalian (or more preferably human) axl receptor proteins, and soluble extracellular fragments thereof which have axl receptor binding activity. Such receptors can be purified from host cells, as described above, which express the same, in accordance with known techniques, or even manufactured synthetically. Specific examples of such receptors include the protein having SEQ ID NO: 2, the protein having SEQ ID NO: 4, and the soluble extracellular fragments thereof.

Soluble mammalian axl receptors which exhibits axl receptor binding activity can be made by deleting the hydrophobic transmembrane region of the native axl receptor. With respect to SEQ ID NO: 1 herein (also referred to herein as axl$^+$), the region coding for the transmembrane domain of the receptor protein is from nucleotide number 1500 to nucleotide number 1574. With respect to SEQ ID NO: 2 herein (also referred to herein as axl$^-$), the region coding for the transmembrane domain of the receptor protein is from nucleotide number 1473 to nucleotide number 1547. By "deletion" is meant removal or alteration of a sufficient portion of the hydrophobic transmembrane domain to render the coded-for receptor soluble in an aqueous solution. In addition, soluble axl receptors can be made from the extracellular portion of a mammalian axl receptor protein as disclosed herein, with the extracellular portion comprising the portion coded for by the domain 5' to the transmembrane domain of the axl oncogene.

Soluble axl receptors may be used in a variety of ways. They may be used for therapeutic purposes, administered to block or stimulate the function of the in situ axl protein, along the same lines disclosed in PCT Application No. WO9015870 with respect to the IL-7 receptor. They may be provided in an aqueous solution, solubilzed therein, to screen for axl receptor binding ligands, or immobilized on a solid support such as dextrose or silica to provide an affinity column which can be used to bind axl receptor binding ligands. The soluble receptor can be labelled with a detectable group such as an alkaline phosphatase in the manner described by J. Flanagan and P. Leder, *Cell* 63, 185–194 (1990), to seek out a membrane-bound ligand for the axl receptor in an immunohistochemical procedure. Other detectable groups can be employed, and the term "labelled" is used herein to refer to the conjugating or covalent bonding of any suitable detectable group, including enzymes (e.g., horseradish peroxidase, β-glucuronidase, alkaline phosphatase, and β-D-galactosidase), fluorescent labels (e.g., fluorescein, luciferase), and radiolabels (e.g. $^{14}$C, $^{131}$I, $^{3}$H, $^{32}$P, and $^{35}$S) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

The axl oncogenes disclosed herein can be used to construct chimeric proteins which are useful for, among other things, detecting the binding of axl receptor ligands. Such chimeric proteins can be made with a recombinant DNA construct which codes for the chimeric protein. The construct comprises (a) an an axl receptor extracellular portion having axl receptor binding activity operatively associated with (b) an effector portion capable of generating a detectable signal upon binding of a ligand to the axl receptor extracellular portion. Suitable effector portions are the enzymatic domain of a membrane bound kinase, such as the enzymatic portion of an epidermal growth factor receptor. The chimeric protein is expressed in a suitable host cell in accordance with the techniques described above so that, when an axl receptor ligand is contacted to the host cell (or a membrane fraction thereof), a detectable signal such as enzymatic activity is generated through activation of the effector portion.

Antibodies which specifically bind to the axl receptor (i.e., antibodies which bind to a single antigenic site or epitope on the axl receptor) are useful for a variety of diagnostic and therapeutic purposes. Such antibodies may be polyclonal or monoclonal in origin, but are preferably of monoclonal origin. The antibodies are preferably IgG antibodies of any suitable species, such as rat, rabbit, or horse, but are generally of mammalian origin. Fragments of IgG antibodies which retain the ability to specifically bind the axl receptor, such as $F(ab')_2$, $F(ab')$, and Fab fragments, are intended to be encompassed by the term "antibody" herein. The antibodies may be chimeric, as described by M. Walker et al., *Molecular Immunol.* 26, 403 (1989). Preferred are antibodies which specifically bind to the extracellular domain of the axl receptor.

Monoclonal antibodies which bind to axl are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., Generation of a Large Combinatorial Library of the Immunoglobulin Repertoire in Phage Lambda, *Science* 246, 1275 (1989).

An antibody as described above which is capable of inhibiting axl receptor function may be used for therapeutic purposes or in vitro diagnostic purposes, along the lines described in R. Hudziak et al., PCT Appln WO 89/06692. Inhibition can be achieved with an antibody which blocks receptor function (i.e., an antagonist), or with an antibody that stimulates receptor function (i.e., an agonist) through downregulation. Antibodies which specifically bind the extracellular domain of the axl receptor may be conjugated to thericin aA chain in the manner described by Vitetta et al., *Science* 238, 1098 (1987).

Diagnostic assays for detecting a tumor generally comprise the steps of, first, contacting cells to antibodies capable of specifically binding the axl receptor, particularly the extracellular domain of the axl receptor, and determining the extend of binding of said antibodies to said cells. The antibody is preferably labelled, as discussed above, to facilitate the detection of binding. Any suitable immunoassay procedure may be employed, such as radioimmunoassay, immunofluorescence, precipitation, agglutination, complement fixation, and enzyme-linked immunosorbent assay. When the cells to be tested remain within the body of a mammal, the antibodies are labelled with a radioactive detectable group and administered to the mammal, and the extend of binding of the antibodies to the cells is observed by external scanning for radioactivity. Further, cells may be screened with a set of two different antibodies, one member of the set selectively binding $axl^-$ receptors and the other member of the set selectively binding $axl^+$ receptors, to diagnose the differential levels of expression of these two receptors. As discussed above, while any type of antibody may be employed for the foregoing diagnostic purposes, monoclonal antibodies are preferred.

EXAMPLES

The examples set forth below are for illustrative purposes only, and are not to be taken as limiting of the present invention.

Amino acid sequences disclosed herein are presented in the amino to carboxy direction, from left to right. The amino and carboxy groups are not presented in the sequence.

Nucleotide sequences are presented herein by single strand only, in the 5' to 3' direction, from left to right.

I. MATERIALS AND METHODS

Identification of a transforming gene in CML cells. Transfections and nude mouse tumorigenicity assays were performed as described previously. See E. Liu et al., *Proc. Natl Acad. Sci. U.S.A.* 85:1952 (1988). The cell lines AF6295 and AF3642 were derived from secondary nude mouse tumors arising from transfection of DNA from blast crisis and chronic phase CML patients, respectively. Tumors were isolated from nude mice and digested in the presence of trypsin-EDTA. A portion of these cells was then plated in plastic tissue culture flasks.

Isolation of cosmids containing eDNA clones. DNA fragments for cosmid cloning were generated by partial MboI digests of genomic DNA from a secondary nude mouse tumor cell line, AF6295. The restricted DNA fragments were size selected on sodium chloride gradients and cloned in the c2RB cosmid vector as previously described. P. Bates, in Enzymology, vol 153. Academic Press, New York, N.Y. (1987). Following ligation, recombinants were packaged with Gigapack gold (Stratagens, LaJolla, Calif.) according to manufacturer's recommendations and used to infect *E. coli* strain W46-4. The cosmid library was screened using the Blur8 probe which contains human Alu repetitive sequences (W. Jelinek et al., *Proc. Natl. Acad. Sci. U.S.A.* 77:1398 (1980)) resulting in the identification of two Alu positive clones, 1-1 and 4-2.

Unique human exon fragments were identified by differential screening of Southern blots of cosmid clones 1-1 and 4-2. Poly-A$^+$ RNA from both AF6295 and untransformed NIH/3T3 cells was obtained as previously described. See F. Ausubel et al., Current Protocols in Molecular Biology. Greene Publishing Associates and Wiley-Interscience, New York, N.Y. (1989). First strand cDNA reactions were performed in a 50 ml final volume of 0.6 mM dCTP, 1 mM each of dATT, dGTT, dTTP, 10 mM DTT, 20 U RNasin, 100 mg/ml random hexamers (Pharmacia, Piscataway, N.J.), 100 mCi $^{32}$P dCTP [3000 Ci/mM (Dupont/NEN)], 1x reverse transcriptass buffer (50 mM Tris, pH 8.3, 50 mM KCl, 10 mM MgCl$_2$, 1 mM DTT, 1 mM EDTA, 100 mg/ml bovine serum albumin), 20 U AMV reverse transcriptase (Promega, Madison, Wis.) and 200 ng poly-A$^+$ mRNA. The mixture was incubated at 42° C. for 45 minutes and denatured at 95° C. for 5 minutes. Unincorporated label was separated on a Sepharose G-50 column. The resulting probes were used for Southern hybridization (see, e.g., F. Ausubel et al., supra) using sheared and denatured mouse or human DNA at 100 mg/ml and salmon sperm DNA at 100 mg/ml for blocking. In addition, Southerns blots were also hybridized with Blur8 to identify fragments from the cosmid clones containing Alu repeat sequences. A single 2.8 kb EcoRI/BamHI fragment (pcc-1) in cosmid clone 1-1 was found to be free of Alu and mouse sequences while containing transcribed exons from the putative human transforming gene.

Production of cDNA libraries. cDNA libraries were constructed in λgt10 using poly-A$^+$ RNA from AF6295. Using pcc-1 as probe, several cDNAs were identified. Sequence analysis of these cDNAs indicated these clones were short (approximately 1 kb in size), and did not contain poly-A$^+$ tails. A full-length cDNA, clone 1-4, was then isolated from a size-selected, oligo-dT primed cDNA library constructed as described (U. Gubler and B. Hoffman, Gene 25:263 (1983)) except as follows: 4 mg of Poly A$^+$ RNA was reverse transcribed using the Superscript M-MuLV (Bethesda Research Laboratories, Gaithersburg, Md.). After second strand synthesis, cDNA products were fractionated on a 0.8% agarose gel in 1xTAE [0.04M Tris-acetate/0.002M EDTA]. Products in the range of 2.7 to 6 kb were electrophoresed onto NA-45 paper (Schleicher and Schuell, Keene, N.H.) and then eluted with 2×250 ml Elution buffer [1 M NaCl/50 mM arginine, free base]. The eluate was extracted three times with phenol:chloroform (1:1) and ethanol precipitated. cDNA products were ligated in EcoRI cut λgt10 arms (Stratagene, La Jolla, Calif.), packaged into phage heads with Gigapack Gold (Stratagene, La Jolla, Calif.) and then plated on C600Hfl E. coli. Recombinants were screened with an axl specific cDNA. Positive clones were subcloned into pBluescript II KS (Stratagene, La Jolla, Calif.) for subsequent sequence analysis.

Normal axl cDNA clones were isolated as described above using a size-selected cDNA library constructed from poly-A+ RNA from the normal human diploid fibroblast cell IMR-90. Recombinant phage were screened using a PCR probe generated from clone 1-4 DNA using primers PJA-14 (bp 2090-2109), GCCCACTCAGATGCTAGTGA and PJA-17 (bp 2569-2588) CAAGGCCTTCAGTGTGTTCT. Positive clones were subcloned into pBluescript II KS for subsequent sequence analysis.

DNA sequencing. Complete sequence from both strands was determined by the dideoxy termination method (F. Sanger et al., Proc. Natl. Acad. Sci. U.S.A. 74:5463 (1977)) using the modified T7 polymerase (Sequenase; United States Biochemical, Cleveland, Ohio). Overlapping fragments for sequence analysis were generated by digestion with exonuclease III (S. Henikoff, in R. Wu (ed) Methods in Enzymology, vol 155. (Academic Press, New York, N.Y. 1987)) or by priming with sequence-specific oligonucleotides. Sequences were compared with the BESTFIT DNA sequence analysis program [University of Wisconsin Genetics Computer Group (J. Devereux et al., Nucl. Acids Res. 12:387 (1984))].

RMA-POR analysis of axl expression. RNA (100 ng of mRNA or 1 mg of total) was denatured at 95° C. for 3–5 minutes in the presence of 100 pmol random hexamers (Pharmacia) and cooled on ice for 2 minutes. The RNA was reverse transcribed in a 20 ml final volume of 1x PCR buffer [10 mM Tris, pH 8.3, 50 mM KCl, 1.5 mM MgCl$_2$, 0.001% gelatin], 625 mM of each dNTP, 20 U RNasin (Promega), 10 mM DTT and 200 U M-MuLV Superscript reverse transcriptase (BRL). The reaction was incubated 10 minutes at room temperature, 45 minutes at 42° C. and 5 minutes at 95° C. One microliter of cDNA product was PCR amplified in a 50 ml final volume of 10 mM Tris, pH 8.3, 50 mM KCl, 1.5 mM MgCl$_2$, 200 mM of each dNTP 0.001% gelatin, 0.5 mM each primer and 1.25 U Taq polymerase (Promega) for 30 cycles under the following conditions: 5 minute at 94° C. 1 minute 55° C. 1.5 minutes at 72° C. for 1 cycle; 1 minute 94° C. 1 minute 55° C. 1.5 minutes 72° C. for 28 cycles; 1 minute 94° C. 10 minutes 60° C. Differential PCR (A. Neubauer et al., Nucl. Acids Res. 18:993 (1990)) was performed using α-actin as a reference. Ten percent of this reaction was electrophoresed on a 12% polyacrylamide gel and stained with ethidium bromide. Primer sequences are as follows: PJA-2 (bp 1847-1866), GGTGGCTGTGAAGAC-GATGA; PJA-3 (bp 2149-2130), CTCAGATACTCCAT-GCCACT; PJA-8 (bp 1320-1339), GAGGTGACCCTG-GAGCTGCA; JB-2 (bp 1490-1471), AGGAGTTGAAGGTCCCTTCA; 5' α-actin, CCTTC-CTGGGCATGGAGTCCT (SEQ ID NO: 5); 3' α-actin, GGAGCAATGATCTTGATCTTC (SEQ ID NO: 6).

Chromosomal localization and fluorescence in situ chromosomal hybridization. A Southern blot of DNA from human/hamster somatic cell hybrids (BIOS, New Haven, Conn.) was probed with random-primer labelled cDNA clones 12-1, 1-4 and genomic clone pcc-1 under conditions recommended by the manufacturer. The filter was washed twice in 2x SSC, 0.5% SDS for 10 minutes at room temperature, once in 1x SSC, 1.0% SDS for 15 minutes at 65° C. twice in 0.1xSSC, 1.0% SDS for 15 minutes at 65° C. and exposed overnight at −70° C.

For in situ hybridization, human metaphase cells were prepared from phytohemagglutinin-stimulated peripheral blood lymphocytes. The axl probe was cosmid 1-1 containing a 41 kb genomic fragment cloned in the cosmid vector c2RB. The procedure used for fluorescence in situ hybridization is a modification of the method described by P. Lichter et al., Human Genet. 80:224 (1988). Biotin-labelled probes were prepared by nick-translation using Bio-11-dUTP (Enzo Diagnostics, New York, N.Y.). Chromosomal DNA was denatured by immersion of the slides in 70% formamide-4xSSC, pH 7.0 at 70° C. for two minutes. Prior to hybridization, unlabelled, sonicated, total human genomic DNA (150 mg/ml) was added to the hybridization mixture (50% formamide, 1xSSC, 10% dextran sulfate, pH 7.0) containing the labelled probe (50–100 ng). The hybridization mixture was heated at 75° C. for 5 minutes, then incubated at 37° C. for 5–10 minutes to promote partial reannealing. After hybridization, the slides were washed in 50% formamide-4xSSC (3 washes, 5 minutes each) at 40° C. followed by three washes in 4xSSC at 40° C. (3 minutes each).

Detection reagents were prepared in 4xSSC, 0.1% TritonX-100, 1% BSA and the washes were performed in 4xSSC, 0.1% TritonX-100 at 40° C. (3 washes, 3 minutes each). For the detection of the labelled probe, slides were incubated with 5 mg/ml fluorescein isothiocyanate (FITC)-conjugated avidin at 37° C. for 30 minutes (Vector Laboratories, Burlingame, Calif.), followed by washes. Metaphase cells were counterstained with 4,6-diamidino-2-phenylindole-dihydrochloride (DAPI, Sigma, St. Louis, Mo.; 200 ng/ml in 2xSSC, 5 minutes, room temperature) and mounted in 20 mM Tris-HCl, pH 8.0, 90% glycerol containing 2.3% DABCO antifade (Sigma). The slides were examined using a Zeiss microscope equipped with epifluorescence optics.

Hybridization analysis. Northern and Southern analysis was performed according to standard protocols (see F. Ausubel et al., supra). RNAs were isolated from cell lines by the methods of Glisin et. al. (Biochemistry 13:2633 (1974)) or Chomczynski and Sacchi (Anal. Biochem. 162:156 (1987)). Radiolabelled probes were generated by the random priming technique or PCR (A. Feinberg and B. Vogelstein, Anal. Biochem. 132:6 (1983); R. Jansen and F. Ledley, Gene. Anal. Techn. 6:79 (1989)) using primers PJA-2 and PJA-3 (see above); PJA-8 (see above) and PJA-9 (bp 1890-1871), CTGACCTCGTGCAGATGGCA; PJA-11 (bp 646-627), TGAGCTTGGCAGCTCAGGTT and PJA-12 (bp 248-267), GCAGGCTGAAGAAAGTCCCT; PJA-14 (bp 2090-2109), GCCCACTCAGATGCTAGTGA and PJA-17 (bp 2569-2588), CAAGGCCTTCAGTGTGTTCT.

Transfection and tumorigenicity assays A 100 mm dish of NIH/3T3 cells containing approximately $5\times10^5$ cells was fed with fresh media 4–24 hours prior to transfection. Five micrograms of plasmid DNA was precipitated with 3M sodium acetate in the presence of 30 mg high molecular weight salmon sperm DNA in a 100 ml volume. The resulting precipitate was resuspended in 450 ml $H_2O$ and incubated overnight at 37° C. with gentle rocking. On the following day, 50 ml 2.5M $CaCl_2$ was added dropwise while bubbling air through a plugged pipette. This solution was then added dropwise to 500 ml of 2xHBS (280 mM NaCl, 50 mM HEPES, 1.5 mM $Na_2HPO_4.12H_2O$, pH 7.05) while bubbling air through a plugged pipette. This solution was allowed to stand for 20–30 minutes at room temperature without agitation. The fine precipitate was then exposed to 3T3 cells for 8 hours at 37° C. The media was removed and 2 mls 15% glycerol (v/v) in phosphate buffered saline (PBS) was added to cells for 90 seconds. Cells were washed with PBS and fed with fresh media. After 24–48 hours, cells were split 1:4 into 100 mm dishes containing 600 mg/ml G418 (total drug). Emergent colonies were then pooled to produce the non-clonal cell lines used in subsequent analysis (TF14A & TF14B-transfected with axl$^+$ sense construct; TF15A & TF15B-transfected with axl$^+$ anti-sense construct; TF16A & TF16B-transfected with pLXSN vector).

For analysis of transformation, half of the pooled G418 resistant cells were passaged once, grown to confluence and scored for focus formation after 2–3 weeks. The remainder of these cells were expanded and injected into the flanks of athymic nude mice at concentrations of $1\times10^5$ and $5\times10^5$ cells per site. Tumor formation was scored 50 days after injection.

Baculovirus expression. The baculovirus transfer vector, pBlueBac (Invitrogen, San Diego, Calif.) contains a β-galactosidase expression cassette which permits recombinant plaque screening by addition of the chromagenic substrate X-gal (5-bromo-4-chloro-3-indolyl-β-D-galactoside; 0.15 mg/ml) to the agarose overlay. The cDNA insertion site of pBlueBac is an NheI site. An axl cDNA segment with full-length coding sequence and NheI compatible ends was produced by cutting the axl cDNA clone 1-4 at the translation start site with NcoI. The resulting 3' overhangs were filled in using the Klenow fragment of DNA pol I plus dNTPs. After heat inactivation, the fragment was digested with EcoR1, ligated into SmaI/EcoR1 digested pBluescriptII-KS plasmid and then used to transform E. coli. The resulting plasmid contains an SpeI site 12 bp upstream of the axl ATG start site and an XbaI site 265 bp downstream of the translation stop site. This SpeI-XbaI fragment was cloned into NheI-digested pBlueBac. The resulting axl transfer vector and wild type (WT) AcNPV DNA were co-transfected into Sf9 cells (M. Summers et al., in Bulletin No. 1555. Texas Agriculture Experiment Station and Texas A&M University, College Station, Tex. (1987)). Subsequent plaque selection yielded the recombinant virus axl-B1Bac. Positives were evaluated for the presence of axl sequences with PCR using primer pairs PJA-5 (bp 951-970), TCA-GACGATGGGATGGGCAT and PJA-6 (bp 1006-1025), CACGGATGCTTGCGAGGTGA; or PJA19 (bp 2755-2774), ATGTCCTCTGCCCTTCCACA; and PJ-7 (bp 2827-2843), TCAGGCACCATCCTCCT.

Immunoblot analysis of axl expression. For analysis of baculovirus expression, Sf9 cells were grown at 27° C. in monolayers ($2\times10^6$ cells/60 mm dish) in TMN-FH media (Invitrogen) and infected with WT or axl-B1Bac virus at a multiplicity of infection greater than 10. After 1, 2, and 3 days the dishes were placed on ice and the cell monolayers were rapidly rinsed with PBS, lysed and then scraped in 0.3 ml of RIPA buffer (50 mM Tris-HCl pH 7.4, 150 mM NaCl, 5 mM EDTA, 1% Triton-X 100, 1% sodium deoxycholate, 0.1% sodium dodecylsulfate (SDS), 100 mM $Na_3VO_4$, 0.5 mM PMSF, and 2.5 mM p-nitrophenylphosphate). After addition of 0.15 ml of 3x Laemmli gel sample loading buffer (30 mM Tris-HCl, pH 7.8, 9% SDS, 15% glycerol, 6% 2-mercaptoethanol and 0.05% bromophenol blue) and boiling 5 minutes at 100° C. 50 ml aliquots of the samples were electrophoresed on 9% SDS-polyacrylamide gels. The proteins were electrotransfered from the gel onto PVDF membrane (Immobilon-P, Millipore, Bedford, Mass.). The membrane was treated for 30 min with 150 mM NaCl, 10 mM Tris-HCl pH 7.5, 0.05% Tween-20 (TBST) containing 1% bovine serum albumin. The blot was then incubated for 1 hr with anti-phosphotyrosine monoclonal antibody (PT-66; Sigma) diluted 1:2000 in TBST. Using a duplicate blot, 1 mM phenylphosphate was included with the anti-phosphotyrosine antibody to block specific binding to phosphotyrosine. The blot was rinsed three times for 5 minute with TBST and then incubated with antimouse IgG-alkaline phosphatase conjugate (A-5153; Sigma) diluted 1:2000 in TBST for 45 min. After 3 rinses in TBST, the blot was incubated with the chromagenic substrates (0.33 mg/ml NBT, 0.165 mg/ml BCIP) in alkaline buffer (100 mM Tris pH 9.5, 100 mMNaCl, 10 mM $MgCl_2$) for 5–20 min. Color development was stopped by rinsing with deionized water. Analysis of tyrosine phosphorylated proteins in the axl-transformed 3T3 cells was performed according to previous protocols (B. McCune and H. Earp, J. Biol. Chem. 264:15501 (1989)).

The polyclonal anti-axl antiserum was prepared by immunizing rabbits with gel-purified baculovirus-expressed axl protein. The antigen in the form of Coomassie-stained gel slice was processed and administered in primary and (after one month) boost injections (E. Harlow and D. Lane, Antibodies: a laboratory manual (Cold Spring Harbor Laboratory, Cold Spring Harbor, N.Y. 1988)). The anti-axl serum was collected 25 days following the boost injection. Immunoblot analysis was performed with the anti-axl antiserum and pre-immune serum diluted 1:3000 in TBST. Anti-rabbit IgG alkaline phosphatase conjugate was used as the secondary antibody.

II. RESULTS

Cloning of the transforming axl gene. In our previous study, using a sensitive NIH/3T3 transfection/tumorigenicity assay, we identified a transforming gene in the DNA from the peripheral leukocytes of two CML patients that lacked ras mutations (E. Liu, supra). The resulting tumors arising from secondary transfection of tumor DNA gave rise to two explant tumor cell lines (AF6295 and AF3642) which harbored the same unique transforming human sequences. Several cosmid clones bearing human Alu repeats were isolated from a cosmid library derived from the DNA of one such explant tumor cell line, AF6295 (see Materials and Methods). Exon mapping identified a genomic fragment, pcc-1, that contained transcribed human sequences but was devoid of Alu repeats and mouse exons. Using pcc-1 as a probe on Northern blots, two axl mRNA species of 5.0 and 3.4 kb were identified in the explant 3T3 cell lines from the CML transfectants, but not in untransformed NIH/3T3 cells or in 3T3 cells transformed by a mutant H-ras oncogene (data not shown). Using pcc-1 as a probe, several axl-specific cDNA clones were isolated from cDNA libraries derived from AF6295 poly-$A^+$ RNA. All hybridized to the same 5.0 and 3.4 kb transcripts in the nude mouse tumor explant cell lines on Northern blot analysis. Sequence analysis of these cDNAs showed sequences in common with pcc-1. Since the original cDNA clones were short and did not contain poly-$A^+$ tails, a size-selected cDNA library was screened in order to identify full-length cDNAs. Several clones were isolated and found to contain 3.2 kb inserts consistent in size with one of the two axl mRNA species. One of these clones, 1-4, was subcloned and sequenced.

Sequence analysis of axl indicates it is a novel receptor tyrosine kinass. The sequence of 1-4 (SEQ ID NO: 1) predicted a protein of 894 amino acids (SEQ ID NO: 2) with two in-frame methionine residues that are candidate initiating amino acids based on Kozak consensus rules (M. Kozak, Nucleic Acid Res. 15:8125 (1987)). Furthermore, an in-frame termination codon lies 170 bp upstream from the first methionine codon. This methionine marks the beginning of a potential signal sequence of 32 amino acids See G. von Heijne, J. Mol. Biol. 173:243 (1984). A search of the EMBL, Genbank, and NBRF Protein databases indicated that axl is a novel protein tyrosine kinass with homology to many known kinases in particular eph, eck, elk, ros, trk, insulin receptor, insulin-related receptor (IRR), IGF-1 receptor, and sevenless. See P. Bates, in Enzymology, vol 153. Academic Press, New York, N.Y. (1987); Y. Ebina et al., Cell 40:747–758; H. Hirai et al., Science 238:1717 (1987); V. Lhotak et al. Mol. Cell. Bio. 11:2496 (1991); R. Lindberg and T. Hunter, Mol. Cell. Biol 10:6316 (1990); D. Martin-Zanca et al., Mol. Cell. Bio. 9:24 (1989); H. Matsushime et al., Mol. Cell. Biol. 6:3000 (1986); P. Shier et al., J. Biol. Chem 264:14605 (1989); A. Ullrich et al., EMBO-J. 5:2503 (1986). The predicted peptide at amino acids 543–569 contained the consensus sequence GxGxxG . . . (15-20 a.a) . . . AxKxM which functions as the $Mg^{+2}$-ATP binding site for tyrosine kinases. H. Hanks et al., Science 241:42 (1988). At approximately 100 amino acids carboxyl-terminal to the $Mg^{+2}$-ATP binding domain in axl lies the sequence DLAARN . . . (34 a.a) . . . PVKWIAIE which resembles, but is distinct from a consensus sequence specific to tyrosine kinases, DLAARN . . . P(I/V) (K/R)W(T/M)APE. H. Hanks et al., supra. Furthermore, there are two sites at amino acids 779 and 821 in the carboxyl-terminus of axl that are similar to the consensus sequence [(E/D)(E/D)(E/D) (E/D)(E/D)Y(M/V)PMXX, where Y=phosphotyrosine] for a phosphatidylinositol 3-kinase (PtdIns3-kinase) binding site. L. Cantley et al., Cell 64:281 (1991). These observations suggest that axl is a tyrosine kinase that interacts intracellularly with PtdIns 3-kinase.

The amino acids 448 to 472 in axl comprise a hydrophobic region consistent with a transmembrane domain. Within the putative extracellular domain, sequences (a.a. 224-428) amino-terminal to the transmembrane region of axl encode two fibronectin type III (FNIII) repeats. T. Peterson et al., Proc. Natl. Acad. Sci. U.S.A. 80:137 (1983); K. Skorstengaard et al., Eur. J. Biochem. 161:441 (1986). Amino terminal to the FNIII repeats in axl (a.a. 37-212) are two immunoglobulin-like (IgL) repeats. A. Williams and A. Barclay, Ann. Rev. Immunol. 6:381 (1988). Highly conserved cysteine and tryptophan residues are characteristic of IgL domains. In addition, the extracellular domain of axl contains six consensus sites for N-linked glycosylation, NxT/S, predicting that the mature axl protein is glycosylated. The juxtaposition of IgL and FNIII repeats in the extracellular region of axl has not been reported for any known receptor tyrosine kinase, thus making axl unique amongst this class of proteins.

Biologic activity of axl. Using cDNA clone 7-1 as a probe for Southern hybridization with nude mouse tumor DNAs, we detected human axl sequences in the appropriate primary and secondary tumors indicating that axl was the transforming gene passaged with each cycle of transfection (data not shown).

To confirm axl's transforming potential, we constructed retroviral expression vectors containing the full-length axl cDNA (clone 1-4). In these constructs, transcription of axl is under the control of an MoMSV long terminal repeat whereas the neomycin phosphotransferase gene, which confers resistance to the drug G418, is driven by an SV40 promoter. A. Miller and G. Rosman, BioTechniques 7:980 (1989). NIH/3T3 cells were transfected with the axl sense (pL1–4S) or anti-sense (pL1–4AS) constructs or vector alone (pLXSN) and then assayed for transformation in a standard focus formation assay (i.e., without G418 selection). No foci were observed in the focus formation assay. Furthermore, colonies arising after G418 selection did not appear transformed. However, when the G418 resistant colonies were passaged once and allowed to reach confluence, foci emerged in the cells transfected with the pL1-4S ($axl^+$ sense construct) but not the pL1-4AS ($axl^+$ anti-sense construct) or the pLXSN (vector). This suggests that axl alone is necessary but insufficient for transformation in this system and that either a second genetic event or selection for cells overexpressing axl is required for axl to be transforming. Northern analysis was performed on RNA isolated from the initial pooled G418 resistant cells (cell lines TF14A, TF14B, TF15A, TF15B, TF16A and TF16B) and transformed foci cloned from cells transfected with the sense axl cDNA (subclones TF14B1, 14B2, 14B3, 14B7, and 14B10). Expression of the human axl gene was seen in cells transfected by sense (TF14A&B) and anti-sense (TF15A&B) constructs albeit at low levels. However, the axl transformed subclones expressed high levels of axl RNA (data not shown). Thus, the second event in axl transformation appears to be a selection for cells expressing increased levels of axl message indicating that overexpression of axl is necessary for 3T3 transformation.

We next tested the tumorigenic capacity of cells transfected with the genomic axl gene (AF6295) or axl cDNA (clones TF14B1, 14B2, 14B3, 14B7 and 14B10). Injection of either AF6295 or clones TF14B1, TF14B2, TF14B3, TF14B7, or TF14B10, all of which express high levels of axl message, resulted in the emergence of tumors within 9 days.

There appeared to be a rough correlation between a short tumor latency with increased expression of axl RNA and protein further supporting the notion that axl overexpression drives 3T3 transformation. In contrast, the initial axl transfectants (TF14A, TF14B, TF15A, TF15B), vector-transfected NIH/3T3 cells and untransformed NIH/3T3 cells did not form tumors within an incubation period of 50 days except for one of the clones transfected with vector alone (TF16A). This clone formed a tumor after 43 days and therefore represents background tumor formation.

Tyrosine kinase activity of axl. To test whether axl is a tyrosine kinase, we analyzed the phosphotyrosine profile of cells transformed by either genomic axl or an axl cDNA. Using an anti-phosphotyrosine antibody, a novel 140 kd tyrosine phosphorylated protein was seen only in cells transfected with axl and not untransformed or ras-transformed NIH/3T3 cells (data not shown). Furthermore, the level of pp140 correlated with the level of axl RNA in these cells.

To further test the tyrosine kinase activity of axl, recombinant axl protein was expressed in Sf9 insect cells using the baculovirus expression system. In a Coomassie stained polyacrylamide gel of cellular proteins, a novel protein of approximately 104 kd was induced in cells infected with a recombinant baculovirus containing axl cDNA (1-4) which was not present in wild-type infected or uninfected cells. The molecular weight of this recombinant protein corresponds roughly to the predicted size (95 kd) of the unglycosylated axl protein minus the signal peptide as deduced from the amino acid sequence using the PEPTIDESORT program [Genetics Computer Group of the University of Wisconsin (J. Devereux et al., Nucl. Acids Res. 12:387 (1984))]. Using an anti-phosphotyrosine monoclonal antibody in Western blot analysis, we detected a similar 104 kd protein in axl baculovirus-infected cells but not wild-type baculovirus infected or uninfected cells (FIG. 6B). In addition, we also detected a 120 kd protein which we suspect represents a partially glycosylated form of axl.

Cloning and characterization of c-axl. Many oncogenes have been shown to be activated by genomic alterations. We accordingly investigated whether rearrangements or deletions of axl were present in the original patient DNAs from which axl was isolated as compared to DNAs from normal peripheral leukocytes and from the nude mouse tumor lines harboring the human axl oncogene. Using probes corresponding to the kinase, transmembrane, and extracellular domains of the cloned axl cDNA in Southern blot analyses, no rearrangements of axl were detected in either the DNAs from the original CML patients or the nude mouse tumors as compared to DNAs from normal blood (data not shown). Furthermore, Northern blot analysis of axl transcripts from AF6295 and several normal and transformed cell types which also express axl mRNA (A549, A431, IMR-90, HeLa and BG-9) revealed the identical 3.4 and 5.0 kb transcripts making rearrangements and major deletions unlikely.

In order to determine the mechanism by which axl was activated, we cloned cDNAs of the normal axl homologue (c-axl). Using RNA from the normal human fibroblast IMR-90, we cloned a normal axl cDNA (clone 4-9) which appears identical to the transforming clone, 1-4. However, another cDNA clone isolated from the normal fibroblast library, 6-2 (SEQ ID NO: 3), predicted an altered version of axl (SEQ ID NO: 4) which lacked amino acids 429-437 (GQAQPVHQL) and contained a G to A transition at base 1170 resulting in the substitution of a leucine for a glutamic acid. We will refer to the predicted axl transcript from 1-4 as "axl+" and that from 6-2 as "axl−". Reverse polymerase chain reaction analysis of RNA with oligonucleotide primers flanking amino acids 429-437 showed both species of axl message present in the nude mouse tumor cell lines as well as other human cell lines and a primary human fibroblast suggesting that axl+ and axl− are splice variants from the same gene. However, the "axl+" species was overexpressed relative to the "axl−" species at an average ratio of 17:1 in the nude mouse tumor cells lines as compared to normal human fibroblasts which exhibited a ratio of 2:1.

Transforming capacity of axl−. To test the transforming capacity of the axl− cDNA, we expressed clone 6-2 in NIH/3T3 cells using the pLXSN retroviral expression vector. Using the same assay as with 1-4, expression of 6-2 also resulted in the emergence of foci after a single passage of G418 resistant colonies. These data suggest that the activation of axl's transforming capacity is due to overexpression and not to structural changes.

Expression of axl. Using both Northern blot and differential polymerase chain reaction (PCR) analysis on cDNA (F. Ausubel et al., supra, A. Neubauer et al., Nucl. Acids Res. 18:993 (1990)), variable expression of axl was seen in most human cell lines tested including cell lines of epithelial, mesenchymal and hematopoietic origins (Table 1).

TABLE 1

| SAMPLE | | NORTHERN ANALYSIS | PCR ANALYSIS |
|---|---|---|---|
| Nude Mouse Tumor Cell Lines | AF6295[1] | ++++ | ++++ |
|  | AF3642[2] | ++++ | ++++ |
| Hematopoietic Cell Lines: | | | |
| Lymphoid | LAM | N.D. | — |
|  | DHL-4 | — | — |
| Myeloid | | | |
| Promyelocytic | HL60 | — | —[3] |
| AML | SKL1 | — | ++ |
| CML blast phase | KOPM-28 | — | ++ |
|  | EM2 | — | + |
|  | EM3 | — | — |
|  | K562 | — | ++ |
| Primary Hematopoietic Tissues: | NPB 1[4] | N.D. | — |
|  | NPB 2 | — | + |
|  | CML/CP[5] | — | + |
|  | MDS 1[6] | — | — |
|  | MDS 2 | — | + |
| Breast Cell Lines: | MDA-157 | — | — |
|  | MDA-468 | — | +++ |
|  | SK-BR3 | — | — |
|  | BT-20 | — | ++ |
|  | BT-474 | — | + |
|  | MCF-7 | — | + |
|  | 600 PEI | — | ++ |
| Normal Breast Epithelia: | 337 | — | ++ |
| Miscellaneous: | | | |
| Cervical ca. | HELA | +++ | +++ |
| Lung ca. | A549 | +++ | +++ |
| Epidermoid ca. | A431 | +++ | +++ |
| Normal Human Fibroblasts: | WI 38 | — | +++ |
|  | BG-9 | +++ | +++ |
|  | IMR-90 | +++ | +++ |
| Mouse Fibroblast Cell Line: | NIH/3T | + | +++[7] |

[1,2] These cell lines were derived from secondary nude mouse tumors arising from transfection of DNA from [1] a patient with blast crisis CML or [2] a patient with chronic phase CML.
[3] The fragment detected was approximately 600 bp. The sequence of this fragment was distinct from axl and may represent a related kinase.
[4] RNA was extracted from normal peripheral blood leukocytes,
[5] peripheral leukocytes from a patient chronic phase CML, and

TABLE 1-continued

| SAMPLE | NORTHERN ANALYSIS | PCR ANALYSIS |
|---|---|---|

[6]from a patient with myelodysplasia.
[7]Analysis of NIH/3T3 cells was done using only axl primers.
N.D., not determined.

In addition, axl was expressed in normal, non-transformed cells including primary fibroblast and breast epithelium. The near ubiquitous expression of axl suggests an important normal cellular function for this receptor kinase.

Chromosomal localization of axl. Various cDNA fragments of axl were hybridized to a Southern blot of DNAs from human/hamster somatic cell hybrids (BIOS, New Haven, Conn.) to determine the chromosomal position of axl. All results indicated that axl is located on human chromosome 19. To determine the location of the axl gene using an independent method, we used fluorescence in situ chromosomal hybridization of a biotin-labelled axl cosmid clone, 1-1, to normal human metaphase chromosomes. Of 25 cells examined, specific labelling was observed on one (4 cells), two (4 cells), three (11 cells) or all four (6 cells) chromatids of chromosome 19 homologues; the signal was localized to the long arm of this chromosome, at band q13.2. Similar results were obtained in a second hybridization experiment using this probe.

The foregoing examples are illustrative of the present invention, and are not to be construed as limiting thereof. The invention is defined by the following claims, with equivalents of the claims to be included therein.

That which is claimed is:

1. An isolated DNA molecule encoding a mammalian axl receptor which exhibits axl oncogene activity selected from the group consisting of:

(a) an isolated DNA molecule which encodes a human axl oncogene selected from the group consisting of DNA having the sequence given herein as SEQ ID NO: 1 and DNA having the sequence given herein as SEQ ID NO: 3; and (b) isolated DNA differing from the isolated DNAs of (a) above in nucleotide sequence due to the degeneracy of the genetic code, and which encodes an axl receptor.

2. An isolated DNA sequence according to claim 1 which encodes a human axl receptor protein.

3. An isolated DNA molecule which encodes a human axl oncogene selected from the group consisting of DNA having the sequence given herein as SEQ ID NO: 1 and DNA having the sequence given herein as SEQ ID NO: 3.

4. A recombinant DNA molecule having vector DNA and a DNA according to claim 1.

5. A recombinant DNA molecule according to claim 4, wherein said vector DNA comprises a vector selected from the group consisting of plasmids, adenoviruses, and cytomegaloviruses.

6. A recombinant DNA molecule according to claim 4, wherein said vector DNA comprises a baculovirus vector.

7. A host cell containing a recombinant DNA molecule of claim 4 and capable of expressing the encoded protein.

8. A host cell according to claim 7, wherein said host cell is a mammalian cell.

9. A host cell according to claim 7, wherein said host cell is selected from the group consisting of baby hamster kidney cells, mouse cells, human embryo cells, and chinese hamster ovary cells.

10. A host cell according to claim 7, wherein said host cell is an insect cell.

11. A recombinant DNA molecule having vector DNA and a DNA according to claim 3.

12. A recombinant DNA molecule according to claim 11, wherein said vector DNA comprises a vector selected from the group consisting of plasmids, adenoviruses, and cytomegaloviruses.

13. A recombinant DNA molecule according to claim 11, wherein said vector DNA comprises a baculovirus vector.

14. A host cell containing a recombinant DNA molecule of claim 11 and capable of expressing the encoded protein.

15. A host cell according to claim 14, wherein said host cell is a mammalian cell.

16. A host cell according to claim 14, wherein said host cell is selected from the group consisting of baby hamster kidney cells, mouse cells, human embryo cells, and chinese hamster ovary cells.

17. A host cell according to claim 14, wherein said host cell is an insect cell.

* * * * *